(12) United States Patent
Watson et al.

(10) Patent No.: US 10,531,859 B2
(45) Date of Patent: Jan. 14, 2020

(54) COMPONENTS FOR A PRECISION ULTRASONIC SCANNING APPARATUS FOR BODY PARTS

(71) Applicant: ArcScan, Inc., Golden, CO (US)

(72) Inventors: John D. Watson, Evergreen, CO (US); Andrew K. Levien, Morrison, CO (US)

(73) Assignee: ArcScan, Inc., Golden, CO (US)

( * ) Notice: Subject to any disclaimer, the term of this patent is extended or adjusted under 35 U.S.C. 154(b) by 918 days.

(21) Appl. No.: 15/081,549

(22) Filed: Mar. 25, 2016

(65) Prior Publication Data

US 2016/0270762 A1  Sep. 22, 2016

Related U.S. Application Data

(60) Continuation-in-part of application No. 14/278,960, filed on May 15, 2014, which is a division of
(Continued)

(51) Int. Cl.
*A61B 3/10* (2006.01)
*A61B 8/00* (2006.01)
(Continued)

(52) U.S. Cl.
CPC .......... *A61B 8/4461* (2013.01); *A61B 3/1005* (2013.01); *A61B 8/10* (2013.01);
(Continued)

(58) Field of Classification Search
None
See application file for complete search history.

(56) References Cited

U.S. PATENT DOCUMENTS

| 3,371,660 A | 3/1968 | Benson |
| 3,821,891 A | 7/1974 | Collins et al. |

(Continued)

FOREIGN PATENT DOCUMENTS

| CA | 2295431 | 7/2001 |
| CA | 2299483 | 7/2001 |

(Continued)

OTHER PUBLICATIONS

"Campbell-Walsh Urology," Tenth Edition, W.B. Saunders, 2012, ISBN 978-1-4160-6911-9, abstract only, 2 pages.
(Continued)

*Primary Examiner* — Angela M Hoffa
(74) *Attorney, Agent, or Firm* — Sheridan Ross P.C.

(57) ABSTRACT

Embodiments of the present invention are directed to various aspects of imaging systems, including permeable and impermeable barriers separating liquid compartments, one of which contains the object to be imaged and the other an ultrasonic transducer, a fluidic bearing between a transducer carriage and guide supporting the carriage, a linear motor for the carriage, and a location sensing device for the carriage. A method and apparatus are disclosed for performing an ultrasound scan on a body part and specifically an instrument which directly attaches to the surface of the body. This apparatus provides high resolution images and increased depth of imaging for high resolution ultrasound of targeted subsurface body tissues. Targeted tissues may include joints, ocular structures, and internal organs. The method and apparatus stabilize and provide accurate determination of the position of the body part relative to the ultrasound probe.

6 Claims, 17 Drawing Sheets

Related U.S. Application Data application No. 12/347,674, filed on Dec. 31, 2008, now Pat. No. 8,758,252, application No. 15/081,549, which is a continuation-in-part of application No. 13/796,931, filed on Mar. 12, 2013, now abandoned.

(60) Provisional application No. 61/018,606, filed on Jan. 2, 2008, provisional application No. 61/022,449, filed on Jan. 21, 2008, provisional application No. 61/042,141, filed on Apr. 3, 2008, provisional application No. 61/045,447, filed on Apr. 16, 2008, provisional application No. 61/609,626, filed on Mar. 12, 2012, provisional application No. 61/611,903, filed on Mar. 16, 2012.

(51) Int. Cl.
*A61B 8/08* (2006.01)
*A61B 8/10* (2006.01)

(52) U.S. Cl.
CPC .............. *A61B 8/40* (2013.01); *A61B 8/4209* (2013.01); *A61B 8/4254* (2013.01); *A61B 8/4281* (2013.01); *A61B 8/4427* (2013.01); *A61B 8/4263* (2013.01); *A61B 8/483* (2013.01); *A61B 8/5207* (2013.01); *A61B 8/54* (2013.01)

(56) References Cited

U.S. PATENT DOCUMENTS

| | | |
|---|---|---|
| 3,997,793 A | 12/1976 | Rogers et al. |
| 4,092,867 A | 6/1978 | Matzuk |
| 4,114,214 A | 9/1978 | VonHeck |
| 4,154,114 A | 5/1979 | Katz |
| 4,183,249 A | 1/1980 | Anderson |
| 4,206,763 A | 6/1980 | Pedersen |
| 4,227,780 A | 10/1980 | Ohta et al. |
| 4,245,250 A | 1/1981 | Tiemann |
| 4,347,213 A | 8/1982 | Rogers |
| 4,484,569 A | 11/1984 | Driller et al. |
| 4,493,877 A | 1/1985 | Burnett |
| 4,545,385 A | 10/1985 | Pirschel |
| 4,550,607 A | 11/1985 | Maslak et al. |
| 4,564,018 A | 1/1986 | Hutchison et al. |
| 4,807,634 A | 2/1989 | Enjoji et al. |
| 4,815,047 A | 3/1989 | Hart |
| 4,817,432 A | 4/1989 | Wallace et al. |
| 4,823,801 A | 4/1989 | Sakane |
| 4,858,124 A | 8/1989 | Lizzi et al. |
| 4,858,613 A | 8/1989 | Fry et al. |
| 4,930,512 A | 6/1990 | Henriksen et al. |
| 4,932,414 A | 6/1990 | Coleman et al. |
| 5,029,587 A | 7/1991 | Baba et al. |
| 5,079,786 A | 1/1992 | Rojas |
| 5,103,517 A | 4/1992 | Krouskop |
| 5,116,114 A | 5/1992 | Nakamura et al. |
| 5,152,746 A | 10/1992 | Atkinson et al. |
| 5,293,871 A | 3/1994 | Reinstein et al. |
| 5,331,962 A | 7/1994 | Coleman et al. |
| 5,369,454 A | 11/1994 | Reinstein et al. |
| 5,387,180 A | 2/1995 | Lehmer |
| 5,460,179 A | 10/1995 | Okunuki et al. |
| 5,474,070 A | 12/1995 | Ophir et al. |
| 5,487,388 A | 1/1996 | Rello et al. |
| 5,517,991 A | 5/1996 | Herrmann et al. |
| 5,551,432 A | 9/1996 | Iezzi |
| 5,556,169 A | 9/1996 | Parrish et al. |
| 5,614,099 A | 3/1997 | Hirose et al. |
| 5,626,150 A | 5/1997 | Johnson et al. |
| 5,626,594 A | 5/1997 | Smith |
| 5,647,367 A | 7/1997 | Lum et al. |
| 5,671,739 A | 9/1997 | Darrow et al. |
| 5,776,068 A | 7/1998 | Silverman et al. |
| 5,826,583 A | 10/1998 | Wood |
| 5,832,550 A | 11/1998 | Hauger et al. |
| 5,855,207 A | 1/1999 | Moenning et al. |
| 5,906,205 A | 5/1999 | Hiebert |
| 5,966,763 A | 10/1999 | Thomas et al. |
| 5,971,006 A | 10/1999 | Seigerschmidt |
| 6,053,613 A | 4/2000 | Wei et al. |
| 6,145,143 A | 11/2000 | Hicks et al. |
| 6,154,204 A | 11/2000 | Thompson et al. |
| 6,198,956 B1 | 3/2001 | Dunne |
| 6,315,727 B1 | 11/2001 | Coleman et al. |
| 6,318,372 B1 | 11/2001 | Hiebert |
| 6,334,227 B1 | 1/2002 | Larger |
| 6,374,439 B2 | 4/2002 | Heimbrock et al. |
| 6,451,008 B1 | 9/2002 | Frey et al. |
| 6,460,207 B1 | 10/2002 | Papay et al. |
| 6,487,447 B1 | 11/2002 | Weimann et al. |
| 6,491,637 B2 | 12/2002 | Foster et al. |
| 6,574,813 B2 | 6/2003 | Bolden et al. |
| 6,629,929 B1 | 10/2003 | Jago et al. |
| 6,684,433 B2 | 2/2004 | Giori et al. |
| 6,780,153 B2 | 8/2004 | Angelsen et al. |
| 6,837,855 B1 | 1/2005 | Puech |
| 6,868,569 B2 | 3/2005 | VanSteenburg |
| 6,887,203 B2 | 5/2005 | Phillips et al. |
| 6,923,767 B2 | 8/2005 | Saied et al. |
| 6,981,417 B1 | 1/2006 | Oravecz |
| 7,048,690 B2 | 5/2006 | Coleman et al. |
| 7,168,116 B2 | 1/2007 | Reger et al. |
| 7,237,898 B1 | 7/2007 | Hohla |
| 7,356,905 B2 | 4/2008 | Ketterling et al. |
| 7,451,507 B2 | 11/2008 | Brinkerhoff et al. |
| 7,454,024 B2 | 11/2008 | Ketterling et al. |
| 7,474,041 B2 | 1/2009 | Ketterling et al. |
| 7,480,058 B2 | 1/2009 | Zhao et al. |
| 7,611,507 B2 | 11/2009 | Raksi et al. |
| 7,708,342 B2 | 5/2010 | Leach |
| 7,920,909 B2 | 4/2011 | Lyon et al. |
| 8,064,989 B2 | 11/2011 | Brown et al. |
| 8,068,647 B2 | 11/2011 | Lin |
| 8,115,935 B2 | 2/2012 | Everett et al. |
| 8,317,709 B2 | 11/2012 | Eilers et al. |
| 8,475,384 B2 | 7/2013 | Hart et al. |
| 8,496,588 B2 | 7/2013 | Eilers et al. |
| 8,510,883 B2 | 8/2013 | Eilers et al. |
| 8,732,878 B2 | 5/2014 | Eilers et al. |
| 8,758,252 B2 | 6/2014 | Eilers et al. |
| 8,824,743 B2 | 9/2014 | Daigle |
| 9,039,623 B2 | 5/2015 | Eilers et al. |
| 9,149,254 B2 | 10/2015 | Watson |
| 2001/0020200 A1 | 9/2001 | Das et al. |
| 2002/0085173 A1 | 7/2002 | Schippert et al. |
| 2002/0143252 A1 | 10/2002 | Dunne et al. |
| 2003/0142269 A1 | 7/2003 | Cumming |
| 2004/0200754 A1 | 10/2004 | Hagemeier |
| 2004/0220478 A1 | 11/2004 | Wallace et al. |
| 2005/0067494 A1 | 3/2005 | Ito et al. |
| 2005/0120479 A1 | 6/2005 | Habashi et al. |
| 2006/0029525 A1 | 2/2006 | Laugharn, Jr. et al. |
| 2006/0106313 A1 | 5/2006 | Hobson |
| 2006/0241533 A1 | 10/2006 | Geller |
| 2006/0288487 A1 | 12/2006 | Roleder et al. |
| 2007/0051362 A1 | 3/2007 | Sullivan et al. |
| 2007/0083995 A1 | 4/2007 | Purdy et al. |
| 2007/0239020 A1 | 10/2007 | Iinuma et al. |
| 2007/0239030 A1 | 10/2007 | Prager et al. |
| 2007/0276233 A1 | 11/2007 | Besson et al. |
| 2008/0097214 A1 | 4/2008 | Meyers et al. |
| 2008/0146939 A1 | 6/2008 | McMorrow et al. |
| 2008/0161696 A1 | 7/2008 | Schmitt et al. |
| 2009/0088623 A1 | 4/2009 | Vortman et al. |
| 2009/0234369 A1 | 9/2009 | Bax et al. |
| 2009/0318758 A1 | 12/2009 | Farr et al. |
| 2010/0031448 A1 | 2/2010 | Hijkema |
| 2010/0217125 A1 | 8/2010 | Kadokura et al. |
| 2010/0229306 A1 | 9/2010 | Reeder et al. |
| 2010/0249562 A1 | 9/2010 | Zhang |
| 2010/0321697 A1 | 12/2010 | Zheng et al. |
| 2011/0172511 A1 | 7/2011 | Peterson et al. |

(56) References Cited

U.S. PATENT DOCUMENTS

| | | | |
|---|---|---|---|
| 2012/0053459 A1 | 3/2012 | Eilers et al. |
| 2012/0209118 A1 | 8/2012 | Warnking |
| 2012/0320368 A1 | 12/2012 | Jiao |
| 2013/0072755 A1 | 3/2013 | Papania et al. |
| 2013/0085370 A1 | 4/2013 | Friedman |
| 2013/0237826 A1 | 9/2013 | Levien |
| 2013/0310692 A1 | 11/2013 | Watson et al. |
| 2014/0009741 A1 | 1/2014 | Levien et al. |
| 2014/0249422 A1 | 9/2014 | Eilers et al. |
| 2014/0268037 A1 | 9/2014 | Siminou |
| 2014/0371589 A1 | 12/2014 | Nakabayashi |
| 2015/0031998 A1 | 1/2015 | Kyono et al. |
| 2015/0238166 A1 | 8/2015 | Heath et al. |
| 2015/0265243 A1 | 9/2015 | Kelly |
| 2016/0166235 A1 | 6/2016 | Levien et al. |
| 2017/0119345 A1 | 5/2017 | Levien et al. |

FOREIGN PATENT DOCUMENTS

| | | |
|---|---|---|
| CA | 2395203 | 7/2001 |
| CA | 2409234 | 4/2004 |
| JP | 2006-149001 | 6/2006 |
| WO | WO 2013/103167 | 7/2013 |

OTHER PUBLICATIONS

"Information for Manufacturers Seeking Marketing Clearance of Diagnostic Ultrasound Systems and Transducers", 2008, Center for Devices and Radiological Health, 68 pages.
Kim et al., "20 MHz/40 MHz Dual Element Transducers for High Frequency Harmonic Imaging," IEEE Transactions on Ultrasonics, Ferroelectrics and Frequency Control, 2008, vol. 55(12), pp. 2683-2691, 25 pages.
Misaridis et al., "Use of Modulated Excitation Signals in Medical Ultrasound. Part I: Basic Concepts and Expected Benefits," IEEE Transactions on Ultrasonics, Ferroelectrics, and Frequency Control, 2005, vol. 52(2), pp. 177-191.
Sanchez et al., "A Novel Coded Excitation Scheme to Improve Spatial and Contrast Resolution of Quantitative Ultrasound Imaging," IEEE Transactions on Ultrasonics, Ferroelectrics, and Frequency Control, 2009, vol. 56(10), pp. 2111-2123, abstract only, 1 page.
Silverman et al., "High-Frequency Ultrasonic Imaging of the Anterior Segment Using an Annular Array Transducer," Ophthalmology, 2007, vol. 114(4), pp. 816-822, 15 pages.
Song et al., "Coded excitation for ultrasound tissue harmonic imaging," Ultrasonics, received in revised form 18, Dec. 2009, retrieved from journal homepage: www.elsevier.com/locate/ultras, pp. 1-7.
Official Action for U.S. Appl. No. 14/278,960, dated Dec. 27, 2016, 17 pages.
Official Action for U.S. Appl. No. 14/278,960, dated Jun. 22, 2017, 10 pages.
U.S. Appl. No. 12/347,674, filed Dec. 31, 2008 now U.S. Pat. No. 8,758,252.
U.S. Appl. No. 14/278,960, filed May 15, 2014.
U.S. Appl. No. 12/418,392, filed Apr. 3, 2009 now U.S. Pat. No. 8,496,588.
U.S. Appl. No. 12/475,322, filed May 29, 2009 now U.S. Pat. No. 9,039,623.
U.S. Appl. No. 09/914,924, filed Jan. 5, 2002 now U.S. Pat. No. 6,491,637.
U.S. Appl. No. 10/233,598, filed Sep. 4, 2002 now U.S. Pat. No. 6,887,203.
U.S. Appl. No. 12/754,444, filed Apr. 5, 2010 now U.S. Pat. No. 8,510,883.
U.S. Appl. No. 13/969,778, filed Aug. 19, 2013 now U.S. Pat. No. 8,732,878.
U.S. Appl. No. 12/638,661, filed Dec. 15, 2009 now U.S. Pat. No. 8,317,709.
U.S. Appl. No. 13/684,699, filed Nov. 26, 2012 now U.S. Pat. No. 9,149,254.
U.S. Appl. No. 13/796,931, filed Mar. 12, 2013.
U.S. Appl. No. 13/937,948, filed Jul. 9, 2013.
U.S. Appl. No. 15/048,706, filed Feb. 19, 2016.
U.S. Appl. No. 14/630,101, filed Feb. 24, 2015.
Official Action for U.S. Appl. No. 14/278,960, dated May 9, 2018, 27 pages.
Official Action for U.S. Appl. No. 14/278,960, dated May 6, 2016, 12 pages.
U.S. Appl. No. 15/048,706, filed Feb. 19, 2016, Levien et al.
Angelson et al. "Which transducer array is best?" European Journal of Ultrasound, 1995, vol. 2., pp. 151-164.
Binder, "SL-OCT and Ultrasound Support the Need for New Phakic IOL Sizing Strategies," Euro Times, Mar. 2007, p. 11.
Coleman et al., "Ultrasonography of the Eye and Orbit," Second Edition, published by Lippincott Williams & Wilkins, 2006, pp. 1-186.
Izatt et al., "Theory of Optical Coherence Tomography," Chap. 2 of "Optical Coherence Tomography Technology and Applications," Drexler and Fujimoto eds, ISBN:978-3-540-77549-2, 2008, pp. 47-72.
Ketterling, "Design and Fabrication of a 40-MHz Annular Array Transducer," IEEE Transactions on Ultrasonics, Ferroelectrics, and Frequency Control, Apr. 2005, vol. 52, No. 4, pp. 672-681.
Ketterling, "Operational Verification of a 40-MHz Annular Array Transducer," IEEE Transactions on Ultrasonics, Ferroelectrics, and Frequency Control, Mar. 2006, vol. 53, No. 3, pp. 623-630.
Mamou, "Chirp-Coded Excitation Imaging With a High-Frequency Ultrasound Annular Array," IEEE Transactions on Ultrasonics, Ferroelectrics, and Frequency Control, Feb. 2008, vol. 55, No. 2, pp. 508-513.
Pinero et al., "Equivalence, Differences Identified in Biometric Analysis," Cataract & Refractive Surgery Today, Mar. 2008, vol. 3, No. 12, pp. 46-49.
Reinstein et al., "Repeatability of Layered Corneal Pachymetry With the Artemis Very High Frequency Digital Ultrasound Arc-Scanner," J. Refractive Surg., vol. 26(9), 2009, original article, 6 pages.
Reinstein, "Subsurface Screening for Keratoconus—Accurate Measurements of the Epithelial and Stromal Layers Aid in Diagnosis," Cataract and Refractive Surgery Today, May 2007, pp. 88-89.
Roholt, "Sizing the Visian ICL," Cataract and Refractive Surgery Today, May 2007, p. 50.
Silverman et al., "Improved System for Sonographic Imaging and Biometry of the Cornea," J. Ultrasound Med., 1997, vol. 16, pp. 117-124.
International Search Report for International Application No. PCT/US2008/088761, dated May 8, 2009, 4 pages.
Written Opinion for International Application No. PCT/US2009/088671, dated May 8, 2009, 5 pages.
International Preliminary Report on Patentability for International Application No. PCT/US2009/088671, dated Jul. 15, 2010, 7 pages.
Extended Search Report for European Patent Application No. 08870422.6, dated May 31, 2011 9 pages.
Official Action for European Patent Application No. 08870422.6, dated Jun. 17, 2011 1 page.
Official Action (with English translation) for Japanese Patent Application No. 2010-541542, dated Aug. 13, 2013, 8 pages.
International Search Report for International Application No. PCT/US2009/039505, dated Jun. 3, 2009.
International Preliminary Report on Patentability for International Application No. PCT/US2009/039505, dated Oct. 14, 2010, 4 pages.
Written Opinion for International Application No. PCT/US2009/039505, dated Jun. 3, 2009, 7 pages.
Official Action for U.S. Appl. No. 12/347,674, dated Oct. 27, 2011 9 pages Restriction Requirement.
Official Action for U.S. Appl. No. 12/347,674, dated Mar. 2, 2012 10 pages.
Official Action for U.S. Appl. No. 12/347,674, dated Aug. 14, 2012 10 pages.

(56) References Cited

OTHER PUBLICATIONS

Official Action for U.S. Appl. No. 12/347,674, dated Jun. 27, 2013 10 pages.
Notice of Allowance for U.S. Appl. No. 12/347,674, dated Jan. 30, 2014 8 pages.
Official Action for U.S. Appl. No. 12/418,392, dated Aug. 3, 2011 14 pages.
Official Action for U.S. Appl. No. 12/418,392, dated Feb. 1, 2012 22 pages.
Official Action for U.S. Appl. No. 12/418,392, dated Jun. 29, 2012 20 pages.
Notice of Allowance for U.S. Appl. No. 12/418,392, dated Mar. 13, 2013 20 pages.

COMPONENTS FOR A PRECISION ULTRASONIC SCANNING APPARATUS FOR BODY PARTS

CROSS REFERENCE TO RELATED APPLICATION

The present application is a continuation-in-part of U.S. application Ser. No. 14/278,960, filed May 15, 2014, entitled "Innovative Components for an Ultrasonic Arc Scanning Apparatus", which is a divisional of U.S. application Ser. No. 12/347,674, filed Dec. 31, 2008, entitled "Innovative Components for an Ultrasonic Arc Scanning Apparatus", which claims the benefits, under 35 U.S.C. § 119(e), of U.S. Provisional Application Ser. Nos. 61/018,606 entitled "Innovative Components for an Ultrasonic Arc Scanning Apparatus", filed Jan. 2, 2008; 61/022,449 entitled "Innovative Components for an Ultrasonic Arc Scanning Apparatus", filed Jan. 21, 2008; 61/042,141 entitled "Innovative Components for an Ultrasonic Arc Scanning Apparatus", filed Apr. 3, 2008; and 61/045,447 entitled "Innovative Components for an Ultrasonic Arc Scanning Apparatus", filed Apr. 16, 2008, all of which are incorporated herein by these references.

The present application is also a continuation-in-part of U.S. application Ser. No. 13/796,931, filed Mar. 12, 2013, entitled "Precision Ultrasonic Scanner for Body Parts with Extended Imaging Depth", which claims the benefits, under 35 U.S.C. § 119(e), of U.S. Provisional Application Ser. No. 61/609,626 entitled "Ultrasonic Scanner for Body Parts" filed Mar. 12, 2012 and U.S. Provisional Application Ser. No. 61/611,903 entitled "Extension of Imaging Depth for Ultrasonic Scanner" filed Mar. 16, 2012, all of which are incorporated herein by these references.

FIELD

The present invention relates in general to a method and apparatus for performing an ultrasound scan on a body part and specifically to an instrument which directly attaches to the surface of the body yet provides very high resolution images. The present invention includes ultrasonic imaging of biological materials such as the joints, internal organs and ocular structures such as the cornea and natural lens of the eye.

BACKGROUND

Ultrasonic imaging has found use in accurate measurement of structures of the eye, such as, for example, the cornea. Such measurements provide an ophthalmic surgeon valuable information that he can use to guide various surgical procedures performed on the cornea, one of the principal ones being the LASIK procedure for correcting refractive errors. They also provide diagnostic information after surgery has been performed to assess the geometrical location of corneal features such as the LASIK scar. This allows the surgeon to assess post surgical changes in the cornea as the cornea heals and to take steps to correct problems that can develop.

Ultrasonic imaging of the cornea presents a problem not generally encountered in other types of tissue. The corneal surfaces are necessarily smooth and spherically shaped to perform the optical function of focusing light rays. Because the corneal structures are smooth and regular, ultrasonic energy is reflected only in specific directions. In particular, an ultrasound beam from a transducer will only be reflected directly back to that transducer when the beam is aligned perpendicular to the corneal surface. This kind of reflective property is called specular reflection.

Because of the specular property of corneal surfaces, it will be appreciated that special care must be taken to align the transducer with the cornea at each position from which a partial image is to be formed. Ultrasonic imaging of large portions of the cornea can be accomplished by scanning the transducer along the cornea surface while continually adjusting the alignment of the transducer to provide a beam that is always directed toward the cornea's center of curvature.

Corneal imaging and measuring of corneal dimensions require that the scanning motion of the transducer be smooth and precisely aligned. Departures, even as small as 5 microns, of the transducer position from a circular path or of the beam's direction from the center of curvature can significantly degrade the resulting image. Mechanisms for performing the requisite scan alignment are described in U.S. Pat. Nos. 6,491,637 and 5,331,962 which are incorporated herein by reference. The reference "Ultrasonography of the Eye and Orbit", Second Edition, Coleman et al., published by Lippincott Williams & Wilkins, 2006 contains an excellent historical and technical summary of ultrasonic imaging of the eye and is incorporated herein by this reference.

While ultrasonic imaging may be used by ophthalmologists for quantitative analysis of laser refractive surgery, it may also be used for implantation of corneal and phakic lenses, implantation of intraocular lenses and specialty procedures such as glaucoma and cataract treatment.

Except for on-axis measurements, dimensions of eye components behind the iris cannot be determined by optical means. New procedures such as implantation of accommodative lenses may provide nearly perfect vision without spectacles or contact lenses. Implantation of accommodative lenses requires precision measurements of, for example, the lens width for successful lens implantation. Ultrasonic imaging can be used to provide the required accurate images of the lens especially where it attaches to the ciliary muscle which is well off-axis and behind the iris and therefore not accessible to optical imaging.

It must be appreciated that ultrasonic imaging requires a liquid medium to be interposed between the object being imaged and the transducer, which requires in turn that the eye, the transducer, and the path between them be at all times be immersed in a liquid medium. Concern for safety of the cornea introduces the practical requirement that the liquid medium be either pure water or normal saline water solution. In either case, the entire mechanism or major portions of it must be submerged in water for long periods.

Conventional mechanical components for guiding and controlling the motion of the transducer, such as journal, ball or roller bearings, are ill-suited for underwater operation. Films inevitably form on the bearing components, interfering with their smooth operation. Anti-fouling solutions cannot be added to the water because they introduce an unacceptable risk of injury to the patient's eye even if the eye is separated from the main body of the liquid by a thin, ultrasonically transparent barrier. Leaks through the barrier film or accidental perforation of the barrier film are an ever present possibility in a practical clinical device.

There remains, therefore, a need for a versatile scan head and transducer positioning apparatus; a water-proof arc scanning motor; an accurate transducer locator method; a fluid bearing method that can provide smooth scanning motion; and a disposable eyepiece, all of which are necessary for an improved ultrasonic arc scanning apparatus that can provide precision imaging for ophthalmology and optometry applications.

Another challenge for any medical imaging system is to provide the highest possible image resolution while also attaining a high depth of image at a reasonable cost. Optical systems such as optical coherence tomography are compact and cost effective and provide excellent resolution. However, they are only capable of imaging a few millimeters into any opaque tissue surface as the light is rapidly absorbed. Current ultrasound systems are very compact and cost effective and have high tissue penetration depths of 100 mm or more. However, they offer relatively low resolution due to their low range of operating frequencies from about 5 MHz to about 10 MHz. MM systems are well-known imaging systems that provide both high depth of image and high resolution. However, they are characterized by high cost, large size and a costly dedicated infrastructure. High frequency ultrasound systems (from about 20 MHz to about 80 MHz) can provide high resolution but only with a limited image depth.

There remains a further need for a low cost, portable ultrasound imaging system that has substantially higher resolution than currently available devices and yet provides a depth of image of that is of high utility for medical diagnosticians.

SUMMARY

These and other needs are addressed by the present invention. The various embodiments and configurations of the present invention are directed generally to ultrasonic imaging of biological materials such as the cornea and lens of the eye and in particular directed to components for an ultrasonic arc scanning apparatus such as a scan head positioning apparatus, a water-proof arc scanning motor, a fluidic bearing and an eyepiece, all of which can be used to, improve the accuracy, precision and ease of use of an ultrasonic arc scanning apparatus.

In one embodiment, a compact scan head positioning apparatus is disclosed. The function of this apparatus is to position the arc scanning assembly and ultrasonic transducer so that the transducer head is continuously following an arc guide centrated at a desired location. The arc guide has a radius of curvature that is approximately that of the eye component to be scanned. A successful scan often requires that the center of curvature of the arc assembly approximately match the center of curvature of the eye component of interest and that the scan head positioning apparatus be well-positioned to take advantage of the precision of a high-frequency ultrasonic pulse. A portion of the scan head positioning apparatus is installed in ambient air while a second portion of the scan head positioning apparatus containing the arc scanning head is installed in a chamber that is filled with water when operational. Thus, the scan head positioning apparatus should have both translating and rotating seals that function over distances and angles required to achieve the desired positioning of the arc scanning head relative to the component of the patient's eye to be scanned.

In another embodiment, a fluidic bearing mechanism is disclosed. The function of the bearing is to allow smooth motion of the transducer carriage assembly along the arc guide which has been positioned by a scan head positioning apparatus such as described above. A successful scan normally requires that the transducer assembly move smoothly along the arc guide to take advantage of the precision of a high frequency ultrasonic pulse.

In one configuration, the fluidic bearing mechanism is defined by a number of liquid flow passages in one or more of the arcuate guide. The liquid is pressurized to flow through the liquid passages and forms a liquid film along a selected interface between the guide assembly and carriage. A distance between the guide and carriage at the selected interface is greater than in the absence of the pressurized liquid.

In yet another embodiment, a motor capable of being operated safely under water is disclosed. The function of the motor is to move a transducer carriage assembly rapidly back and forth along a normally fixed arc guide so as to allow an ultrasonic scan of an eye component to be made.

In one configuration, the motor includes one or more magnets in one of the carriage and guide, and an iron-containing core surrounded by one or more electric coils in the other of the carriage and guide. In a preferred implementation, first and second magnets are in the carriage, and the electric coil and iron-containing core are in a guide track. The first and second magnets are positioned side-by-side, with the north-south polarities being opposed to one another. A long dimension of the electric coil(s) is adjacent to a face of the magnets to substantially maximize a propelling force. In a particularly preferred implementation, a mass of the carriage ranges from about 0.1 kg to about 0.3 kg. The electric coil is formed by a number of coil segments, with each of a number of subsets of the coil segments being powered selectively and independently by an electric circuit. A force caused by an electric current in a subset of the coil segments and local B-fields of the first and second magnets are in a common direction.

In another embodiment, a carriage location sensing device is provided to determine a location of the carriage relative to the guide assembly. The sensing device can have numerous configurations. In one configuration, the location sensing device includes a position encoder mounted on the carriage. The encoder senses a position of the carriage by reading a magnetic strip positioned along a length of the guide track. In another configuration, the location sensing device includes an optical encoder mounted on the carriage. The optical encoder senses a position of the carriage by illuminating a length of the guide track with light and sensing one or more of a refractive, diffractive, diffusive, and reflective distribution of light. For example, the encoder can illuminate a bar code positioned along a length of the arc guide. The bar code will produce a unique distribution of reflected light at any position along the length of guide. In another configuration, the locating sensing device includes a magnetic field sensor. The sensed magnetic field is related to a position along the guide. In yet another configuration, the location sensing device includes a mechanical counter. The mechanical counter produces a count, which is related to dimensional units and to a position along the guide.

Knowing the position of the carriage as a function of time can provide benefits. In a carriage motor having one or more magnets and an iron-containing core surrounded by electric coil segments, a controller, for example, can, at a selected point in time, selectively energize an electric coil segment in proximity to a sensed position of the carriage. The controller can, additionally or alternatively and at a selected point in time, selectively energize the transducer in response to a sensed position of the carriage to produce a non-uniform, desired physical spacing of ultrasound pulses. Position tracking is particularly beneficial where the carriage has a non-uniform velocity and/or acceleration along the guide. Simply put, the sensing device can provide precise position of the transducer carriage along the arc guide assembly which, in turn, allows for a precise and accurate ultrasonic scan to be made.

In yet another embodiment, three configurations of an eyepiece are disclosed. These all provide an acoustic path for ultrasonic scanning and separate the water in which the patient's eye is immersed, from the water in the chamber in which the positioning and arc guide assembly are contained. These configurations are relatively free from annoying leakage problems, are comfortable to the patient and can be manufactured for a low cost as the eyepiece should be replaced for every new patient. The different configurations incorporate different attachment and sealing mechanisms.

By way of example, a first configuration of an imaging device includes:
(a) an eyepiece for receiving an eye of a patient;
(b) a first liquid chamber in contact with an ultrasonic transducer;
(c) a second liquid chamber in contact with the patient's eye to be imaged by the ultrasonic transducer; and
(d) a barrier separating the first and second liquid chambers, wherein at least one of the following is true:
  (D1) the second liquid chamber comprises a drain port to drain liquid from the first liquid chamber; and
  (D2) the barrier is permeable to the liquid but impermeable to selected biological microbes, the microbes being selected from the group consisting of bacterium, virus, and fungus.

In another embodiment, a second configuration of an imaging device includes an eyepiece that includes a separate face seal ring. The face seal ring is filled with a liquid to better conform to a patient's face.

The present disclosure is also directed towards providing an ultrasound imaging system that is portable. Such a system may be directly attached to the surface of the body and provide high resolution images of targeted subsurface body tissues with image resolution far superior to that of known state of the art ultrasound instruments without the need for a large, fixed and cumbersome instrument as required by other imaging technologies such as X-ray or MRI. Targeted tissues may include but not be limited to joints, ocular structures, and internal organs.

The present disclosure is also directed towards providing an ultrasound imaging system that can produce high image resolution (down to about 100 μm) at depths in the range of about 50 mm to about 60 mm. A number of known techniques are combined in a novel fashion and facilitated by an ultrasound system such as described above that stabilize the body part (or eye in some specific cases) relative to the ultrasound probe. Where the highest precision is required, a means of further elimination of movement due to breathing or heart beat is also disclosed.

An ultrasound scanner system is also disclosed, comprising (1) an instrument body; (2) a linear positioner assembly interconnected to the instrument body; (3) an ultrasound probe which emits and receives an ultrasound pulse, the ultrasound probe interconnected to the linear positioner assembly wherein the ultrasound probe may operate in at least one dimension; (4) an instrument chamber disposed within the body and engaged with a membrane; and (5) a sealing chamber engaged with the membrane and a scanned object, wherein a transducer in the ultrasound probe emits and receives the ultrasound pulse through the instrument chamber, the membrane and the sealing chamber, wherein the ultrasound pulse contacts the scanned object.

A method is disclosed, comprising (1) sealing an ultrasound scanner to a scanned object; (2) filling a sealing chamber in a body of the ultrasound scanner with a sealing chamber fluid to provide a low acoustic impedance interface between the ultrasound scanner and a scanned object surface; (3) emitting and receiving an ultrasound pulse from a transducer contained in an ultrasound probe to generate an ultrasound image of a target matter within the scanned object.

The following definitions are used herein:

An A-scan is representation of the reflected amplitudes of ultrasonic pulses emitted by an ultrasonic transducer as a function of time.

An accommodative lens, also known as a presbyopic lens or presby lens, is an intraocular lens implant that changes its focal distance in response to contraction of the ciliary muscle. When successfully implanted, an accommodative lens reverses presbyopia, the inability of the eye to change its focal distance from far to near.

Aligning means positioning the transducer and transducer carriage guide preferably accurately and reproducibly in space with respect to a feature of the eye component of interest (such as the center of curvature or boundary of the cornea, lens, retina, etcetera).

The anterior chamber comprises the region of the eye from the front of the eye to the iris.

The anterior segment comprises the region of the eye from the front of the eye to just beyond the back of the lens.

An arc scanner is a scanning device where the sensor moves in a substantially precise arc about the center of the area to be scanned with its beam constantly directed through a central point.

Arc scanning transducer center of curvature is the same as the center of curvature of the arc scanning guide.

Auto-centering means automatically, typically under computer control, causing centration of the arc scanning transducer with the eye component of interest.

A B-scan is representation of data as a by converting A-scan data using acoustic velocities to an image of the eye using grayscales which correspond to A-scan amplitudes.

A canthus is the angular junction of the eyelids at either corner of the eye where the upper and lower eyelids meet.

Centration means substantially aligning the center of curvature of the arc scanning transducer in space with the center of curvature of the eye component of interest (such as the cornea, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

Depth of focus is the distance over which the image plane can be displaced while a single object plane remains in acceptably sharp focus. The depth of focus is substantially symmetrical about the image plane when the image plane is at the focal distance.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

The focal length or focal distance of a focused ultrasound system is the distance between the transducer element (which emits an ultrasound pulse from a finite diameter element) and the point where the ultrasound beam diameter is a minimum and generally of maximum amplitude. The beam at this minimum diameter is said to be in focus.

A guide is an apparatus for directing the motion of another apparatus.

Haptics are little curved hair-like protrusions extending from the outer diameter of some types of artificial lenses. These haptics attach these lens to the ciliary muscle by protruding into the ciliary sulcus and allow the lens to accommodate in response to the action of the ciliary muscle.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after exposing it by cutting a thin flap, so as to reshape the external shape of the cornea.

A meridian is a plane that cuts through a portion of a three-dimensional component such as the cornea or natural lens of the eye and its angle is expressed relative to a horizon defined by the canthi.

MRI is magnetic resonance imaging.

The natural lens (also known as the aquula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ocular means having to do with the eye or eyeball.

Ophthalmology means the branch of medicine that deals with the eye.

Optical as used herein refers to processes that use light rays.

The optical axis of the eye is the line of best fit joining the centers of curvature of the refracting surfaces (the anterior and posterior surfaces of the cornea and lens).

Pachymetery or corneal pachymetery is technically referred to as Time Domain Reflectometry ultrasound. A pulse of ultrasonic energy is sent toward the cornea and the time spacing of the returning echoes are used to arrive at corneal thickness.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

The posterior chamber comprises the region of the eye from the back of the iris to the front of the lens.

The posterior segment comprises the region of the eye from the back of the lens to the rear of the eye comprising the retina and optical nerve.

Presbyiopia is typically caused by a loss of elasticity of the natural lens inside the eye. This occurs as part of the ageing process and, although it cannot be 'cured', it can be corrected by wearing glasses or implanting an artificial lens.

Purkinje images are reflections of objects from structure of the eye. There are at least four Purkinje images that are visible on looking at an eye. The first Purkinje image (P1) is the reflection from the outer surface of the cornea. The second Purkinje image (P2) is the reflection from the inner surface of the cornea. The third Purkinje image (P3) is the reflection from the outer (anterior) surface of the lens. The fourth Purkinje image (P4) is the reflection from the inner (posterior) surface of the lens. Unlike the others, P4 is an inverted image. The first and fourth Purkinje images are used by some eye trackers, devices to measure the position of an eye. Purkinje images are named after Czech anatomist Jan Evangelista Purkyně (1787-1869).

Refractive means anything pertaining to the focusing of light rays by the various components of the eye.

Registration means aligning.

Sector scanner is an ultrasonic scanner that sweeps out a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will only be reflected directly back to that transducer when the beam is aligned perpendicular to a specular surface.

The ciliary sulcus is the groove between the iris and ciliary body. The scleral sulcus is a slight groove at the junction of the sclera and cornea.

A track is an apparatus along which another apparatus moves.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

Ultrasound probe means an assembly comprising a transducer element (typically a piezoelectric material), a probe body and electrical conduits that carry transmitted and received signals from the element to an analog-to-digital (A/D) converter external to the probe.

Ultrasound pulse means a group of ultrasound waves centered around a center frequency where the pulse comprises at least one and up to about ten wave cycles. The ultrasound pulse is therefore a short burst of one to about ten wavelengths truncated at both ends of the wave train. An ultrasound pulse is further described in "Ultrasonography of the Eye and Orbit", Second Edition, Coleman et al., published by Lippincott Williams & Wilkins, 2006, which is incorporated herein by reference.

The visual axis of the eye is the line joining the object of interest and the fovea and which passes through the nodal points.

Zonules are tension-able ligaments extending from near the outer diameter of the crystalline lens. The zonules attach the lens to the ciliary body which allows the lens to accommodate in response to the action of the ciliary muscle.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

BRIEF DESCRIPTION OF THE DRAWINGS

The invention may take form in various components and arrangements of components, and in various steps and arrangements of steps. The drawings are only for purposes of illustrating some embodiments and are not to be construed as limiting the invention.

FIG. 13b illustrates a detailed portion of FIG. 13a.

It should be understood that the drawings are not necessarily to scale. In certain instances, details that are not necessary for an understanding of the invention may have been omitted. It should be understood, of course, that the invention is not necessarily limited to the particular embodiments illustrated herein.

DETAILED DESCRIPTION

Precision Ultrasound Scanning for the Eye

The embodiments described herein provide a superior design to prior art arc scanners. The embodiments disclose a scanning mechanism that is normally more tolerant of the underwater environment than prior art arc scanners. According to certain of the embodiments, an ultrasonic transducer is mounted to a transducer carriage that moves along a circularly curved guide. The carriage is typically guided by a guide, which is preferably configured as a track, so that the transducer beam axis is continuously directed towards a fixed center point regardless of the carriage's position along the guide. The guide assembly and the carriage have one or more smooth and precisely conforming surfaces that face one another and support a liquid film between them as described below.

The embodiments described herein are illustrated by an arc scanner in which the guide assembly is formed in the fixed shape of an arc that approximates the curvature of the eye's cornea or anterior lens surface. The guide may also have a variable shape such, as for example, two or more arcs or any continuously curved shape including a linear guide. The guide may also be flexible such that it can be controlled to conform to a desired shape. This latter embodiment would be useful for positioning a transducer carriage such that the transducer is aimed in a desired direction so as to better image any specular or non-specular component in an eye. Such flexing and aiming can be made in response to the changing shape of an eye component being imaged.

Ultrasonic Scanning Principles

Figure 1:
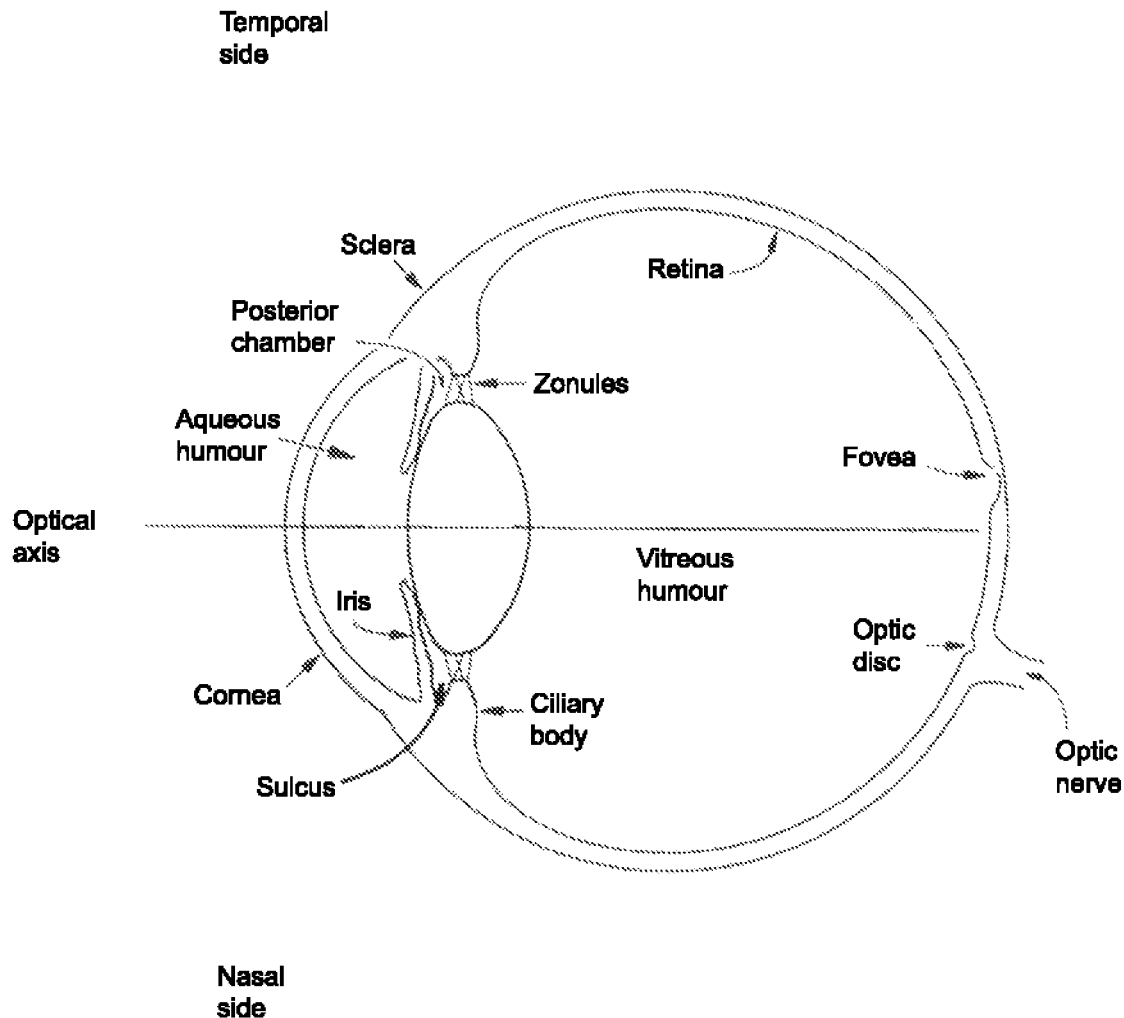
FIG. 1 is a schematic of the main elements of a human eye.

FIG. 1 is a schematic of the main elements of a human eye. The principal refracting components are the cornea, iris and lens. The cornea, which is optically transparent, is located at the front of the eye enclosing front of the anterior chamber. The iris separates the anterior chamber from the posterior chamber. The front of the lens encloses the back side of the posterior chamber. The natural lens sits directly behind the iris. Only the central part of the lens, which is behind the pupil, can be seen optically. The anterior and posterior chambers comprise the anterior segment of the eye. The main volume or posterior segment of the eye lies behind the lens, with the retina and optical nerve at the rear of the posterior segment of the eye. The composition of the eye's aqueous and vitreous humour are very close to that of water with a density of about 1,000 kg/m$^3$, and this allows the eye to be a very good medium for the transmission of acoustic energy.

Optical means are suitable for viewing the anterior chamber and for viewing along the entire central axis of the eye. However, optical means cannot be used to view the portions of the posterior chamber lying immediately behind the iris, which includes the suspensory ligaments (called zonules), ciliary sulci and ciliary body. However, the eye components that cannot be viewed optically, can be viewed with high-frequency acoustic energy. As is well-known, acoustic frequencies in the ultrasonic range of about 10 MHz to about 60 MHz can be used to provide very high resolution images of, for example, the cornea and the lens.

Figure 2A:
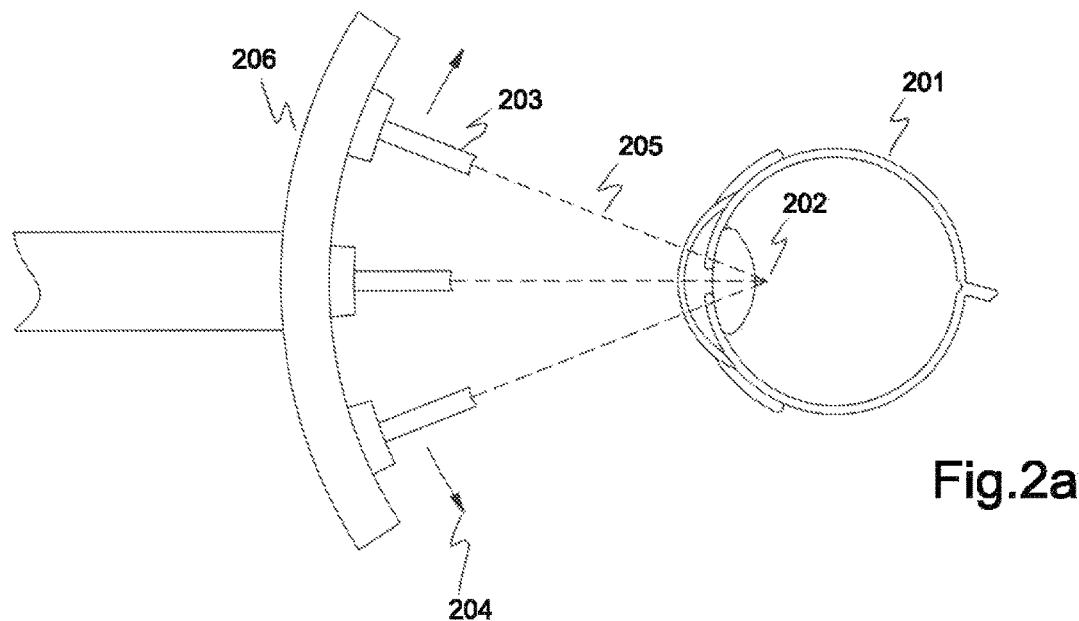
FIG. 2a illustrates an arc scanning principle for ultrasonic scanners.

FIG. 2 illustrates two different types of scanning strategies for ultrasonic scanners capable of imaging most regions of the interior of an eye. FIG. 2a illustrates the arc scanning principle for producing an ultrasonic scan of a component of an eye 201. In this type of scanner, which is described, for example, in U.S. Pat. Nos. 6,315,727, 6,491,637, 6,887,203 and 7,048,690, a transducer is moved in an arc whose center is set at a location of interest in the eye. In FIG. 2a, an ultrasonic transducer 203 is shown in a sequence of positions with the center of curvature of the arc guide 206 at approximately the center of curvature 202 of the cornea. The transducer 203 is moved in an arc as shown to produce many acoustic echoes (represented as rays 205) as it moves 204 along the arc guide which can then be combined to form a cross-sectional image of the eye features of interest.

Figure 2B:
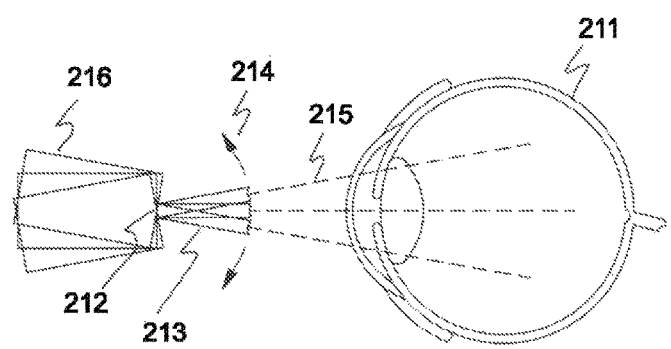
FIG. 2b illustrates a sector scanning principle for ultrasonic scanners.

FIG. 2b illustrates the sector scanning principle for producing an ultrasonic image of a particular location with an eye 211. In this type of hand-held scanner, which is described, for example, in U.S. Pat. No. 6,198, 956, an ultrasonic transducer 213 is shown being oscillated 216 about a fixed position 212 so as to produce 214 many acoustic echoes (represented as rays 215). These echoes can then be combined to form of a localized region of interest within the eye. The scanning principle illustrated in this figure is called sector scanning.

In both the arc and sector ultrasonic scanners, the transducer acts as both the transmitter and receiver of acoustic signals. The transducer emits a short acoustic pulse and then receives the reflected acoustic signal. This technique is described, for example, in U.S. Pat. No. 5,293,871 and in "Ultrasonography of the Eye and Orbit", Second Edition, Coleman et al., published by Lippincott Williams & Wilkins, 2006.

A sector scanner can be used to measure the thickness of an eye component such as, for example, the thickness of the cornea or the thickness of the lens along the optical axis. A sector scanner cannot be used to measure the length of specular features that extend laterally, such as, for example, the length of a LASIK scar, because only that small portion of the cornea that is perpendicular to the acoustic beam and reflects acoustic energy back to the transducer is visible to a sector scanner. With a sector scanner, the patient is typically required to be supine.

An arc scanner, on the other hand, can be used to measure the thickness of an eye component such as, for example, the thickness of the cornea or the thickness of a lens as well as to measure the length of specular features that extend laterally, such as, for example, the length of a LASIK scar or the lateral length of a natural or implanted lens. In an arc scanner, the patient is typically looking downward at approximately 45 degrees from horizontal. This is a preferred position and has relevance to the design of an eyepiece described in FIGS. 10 through 12.

Both arc and sector scanners are discussed on page 35 of "Ultrasonography of the Eye and Orbit", Second Edition, Coleman et al., published by Lippincott Williams & Wilkins, 2006.

Figure 3:
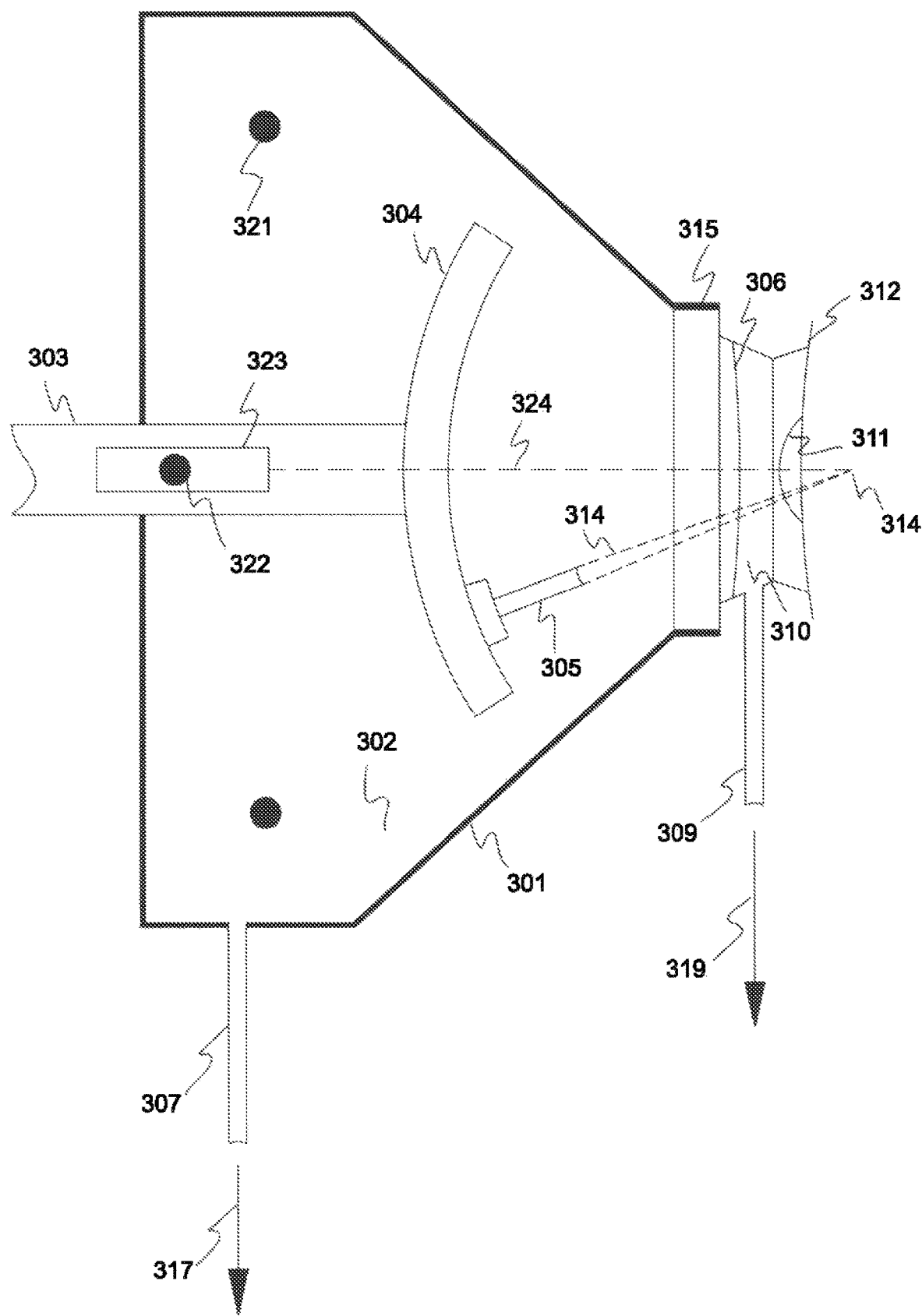
FIG. 3 is a schematic of an arc scanning device.

FIG. 3 shows the main elements of an arc scanning device illustrating positioning of a transducer along an arc guide whose center of curvature is centered approximately on the center of curvature of an eye component of interest. FIG. 3 shows fixation lights 321 and 322 that allow the patient to fixate his or her eye to maintain it in a steady position during scanning. FIG. 3 also shows an optical video camera 323 which may be used by the operator of the arc scanner to monitor the position of the patient's eye along an optical path 324 and to determine whether the patient's eye is open before a scan is initiated. The transducer and its arc guide assembly are immersed in a chamber of water 302 to provide a transmission path 314 for the acoustic signals. The patient's eye must also be immersed in water to provide continuity of the transmission path 314 for the acoustic signal. FIG. 3 also shows a hygienic barrier 306 which separates the water chamber 301, 315 in which the transducer 305 and arc guide assembly 304 are contained from the water 310 in which the patient's eye is immersed. This barrier 306 provides the separation of water 302 in which the transducer 305 and arc track assembly 304 are contained from the water 310 in which the patient's eye is immersed. The arc guide assembly and associated components may be contaminated, for example, by particles from wearing mechanical components. The water 310 in which the patient's eye is immersed may be contaminated by bacteria or virus particles from the patient. As can be appreciated, the water 310 in which the patient's eye is immersed should be changed for every patient to prevent possible disease transmission. As can be further appreciated, the hygienic membrane 306 must be substantially transparent to ultrasound so as to maintain a clear acoustic transmission path between the patient's eye and the ultrasonic transducer. The hygienic membrane 306 is typically formed as part of a disposable eyepiece such as described in FIGS. 10 through 12.

References are made herein to a medium suitable for conducting acoustic energy in the form of ultrasound. There are reasons to prefer that the medium be pure water or physiologic saline (also known as normal saline) but the embodiments do not exclude other media suitable for conducting acoustic energy in the form of ultrasound. Most other media present an increased danger to the patient's eye, even with a barrier interposed between the eye and the ultrasonic transducer. Barriers can leak or be breached, allowing the liquids on either side to mix, thus bringing a potentially harmful material into contact with the eye.

It should be appreciated, however, that non-harmful, less-corrosive media and leakproof, impenetrable barriers might be developed or discovered. This might allow different media than pure water or physiologic saline to be used in this invention. Nothing about embodiments herein other than the hazards just described requires pure water or physiologic saline to be present in the chamber containing the transducer. All references to water in the following should accordingly be understood as referring to any suitable liquid.

FIG. 3 illustrates the continuity of an acoustic transmission path through water. A chamber 301, 315 of water 302 is shown with a positioning arm 303 and arc guide assembly 304 on which an ultrasonic transducer 305 is mounted. An ultrasonically transparent barrier 306 separates chamber 301, 315 from the interior of an eyepiece. The eyepiece contains a separate volume of water 310 which fills the interior of the eyepiece and contacts a patient's eye surface 311. The eyepiece is connected and sealed to the main chamber 301, 315 of the arc scanning device, and is also sealed against the patient's face 312. As can be seen, there is a continuous path through water from the transducer 305 to the patient's eye surface 311 for the efficient passage of acoustic energy. The barrier 306 readily passes acoustic energy without alteration, thus forming a portion of the continuous path between the transducer 305 and the patient's eye surface 311. Since the acoustic impedance of the patient's eye is approximately that of water, the acoustic energy from the transducer can be efficiently transmitted into the eye and reflected back from an eye component, such as for example, the surface of the cornea, to the transducer. Also shown in FIG. 3 are a water fill tube 307 from a reservoir 317 to the main chamber 301, 315 and a separate water fill tube 309 from a reservoir 319 to the eyepiece. As can be appreciated, the water used in the eyepiece can be distilled or slightly saline to match the salinity of the eye, and the water used in the eyepiece can be introduced at a temperature that is comfortable for the patient.

Components of the Present Invention

Scan Head Positioning Apparatus

The function of a scan head positioning apparatus is to position the arc scanning head assembly and ultrasonic transducer so that the transducer head is continuously on an arc guide that is positioned such that its center of curvature is at the approximate center of curvature of the eye component to be scanned. A successful scan often requires that the radius of curvature of the arc assembly approximately match the radius of curvature of the eye component of interest and that the scan head positioning apparatus be accurately positioned to take advantage of the precision of a high frequency ultrasonic pulse.

Figure 4:
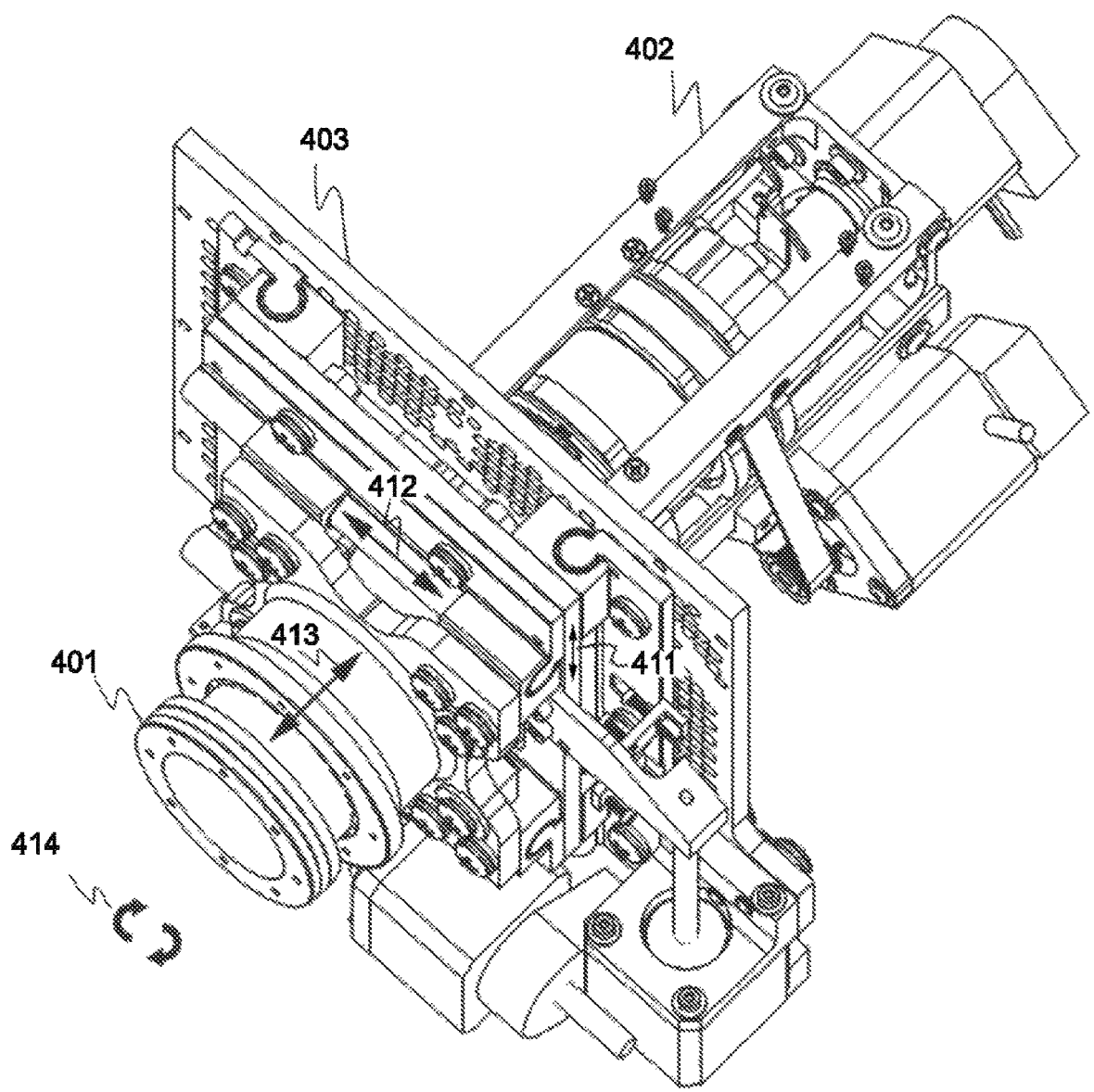
FIG. 4 illustrates an isometric view of a compact arc scanning head positioning mechanism.

FIG. 4 illustrates an isometric view of a compact scan head positioning mechanism. An axial carrier frame 402 and mounting plate 403 are fixed to the main arc scanner assembly. The scanner head mount arm 401 can move axially back and forth as shown by arrow 413. The scanner head mount arm 401 can rotate about its axis as shown by arrows 414. The scanner head mount arm 401 can move up and down as shown by arrows 411 and back and forth as shown by arrows 412. The scan head, which is mounted on the scanner head mount arm 401, is not shown in this figure.

Figure 5:
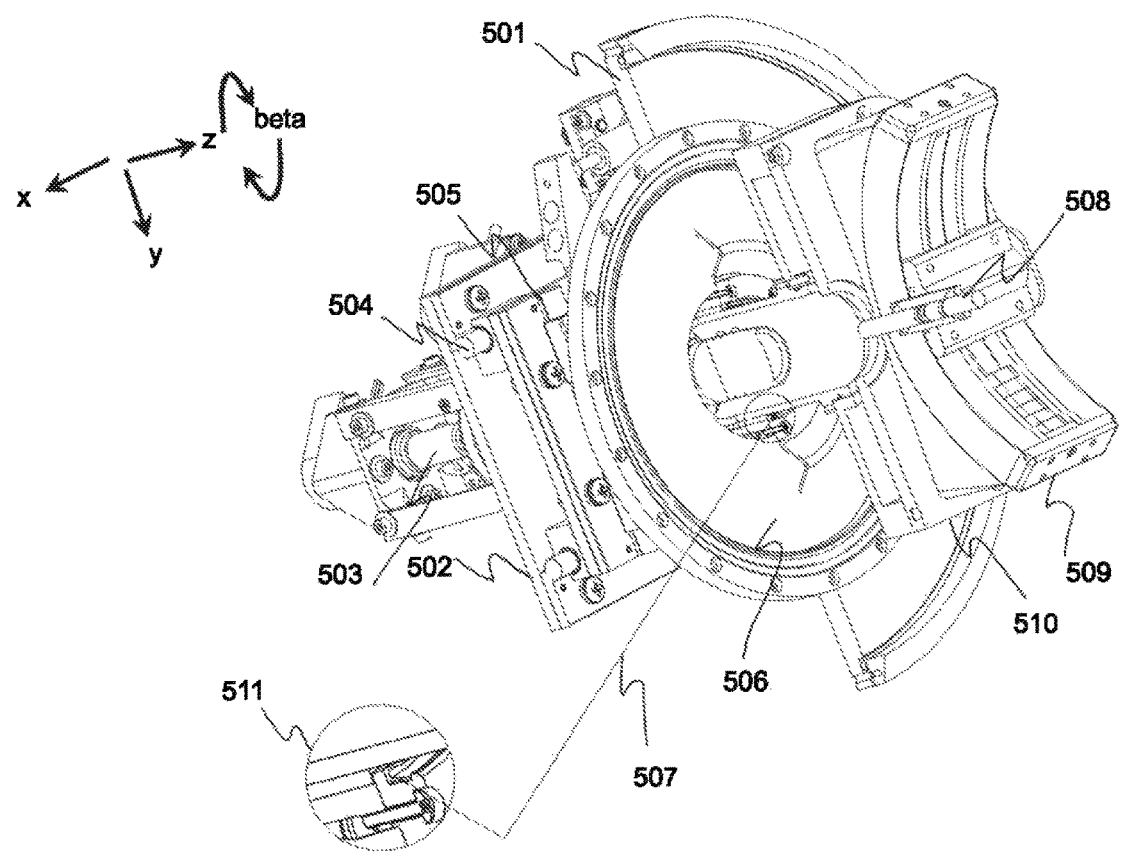
FIG. 5 further illustrates a compact arc scanning head positioning mechanism.

FIG. 5 further illustrates a compact scan head positioning mechanism. FIG. 5 shows an arc scanner head 509 with ultrasonic transducer 508 mounted on the end of a scanner head mount arm 510. These components (scanner head mount arm 510, scanner head 509 and ultrasonic transducer 508) are operative under water and are sealed 511 from the rear portion of the positioning mechanism by a translational seal 506 and a rotational seal 507. The translational seal 506 is preferably formed by a large rubber membrane that can flex with the small x and y motions required by the scanning head positioner, though any sealing mechanism may be employed. The z-axis seal and rotational seal 507 are attached to a stationary plate 501 which is affixed to the main arc scanner assembly. The z-axis and rotational seal 507 is typically formed by a circumferential groove type sealing mechanism with the groove facing into the water, though any sealing mechanism may be employed. The seal is preferably a commercially available seal from SealScience, model 810V. It allows both rotation and axial translation of the center tube while maintaining a water tight seal. The cross section of the seal is such that increased water pressure acts on the seal in a way that increases radial sealing force. The sealing surfaces are preferably anodized aluminum. Stationary plate 502 is also affixed to the main arc scanner assembly. The scanning head can be moved back and forth axially (the z-direction) by axial piston 503 or another suitable mechanism. The scanning head can be rotated (the beta-direction) about the z-axis by a rotary stepping motor (not shown) or another suitable device. The scanning head can be moved up and down (the y-direction) by piston 505 or another suitable mechanism. The scanning head can be moved from side to side (the x-direction) by piston 504 or another suitable mechanism. The components to the left or rear of stationary plate 501 remain in ambient air while the components to the right or font of stationary plate 501 are in immersed in water when the arc scanner is operational.

Magnetic Sensing System

The carriage can be moved along the arc guide using any of a number of motive methods. In the preferred embodiment, the guide track contains windings arranged so that they together with the magnets in the carriage form a linear motor (described below in FIGS. 8 and 9). Also in the preferred embodiment, there is a position encoder, preferably incremental and magnetic, borne by the guide track and the carriage, that allows external circuitry to sense the position of the carriage along the track. The positional information is used to control which windings are energized as the carriage moves along the track. It is also used to trigger the sending of ultrasonic pulses so as to provide, for example, a uniform physical spacing of the pulse-echo tracks in an ultrasound B-scan image. As can be appreciated, the positional information can be used to trigger the sending of ultrasonic pulses so as to provide a non-uniform but desired physical spacing of the pulse-echo tracks in an ultrasound B-scan image.

Figure 6:
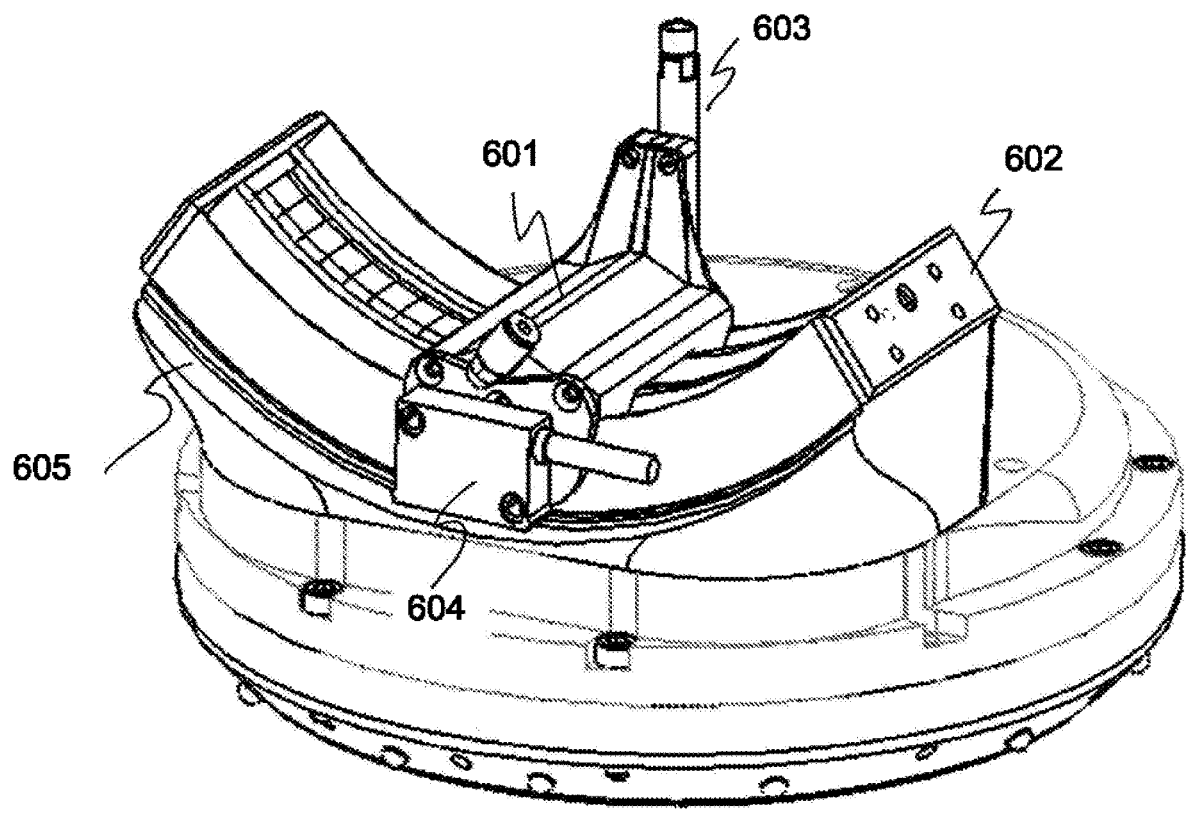
FIG. 6 illustrates a magnetic positioning system.

FIG. 6 illustrates a magnetic positioning system. This positioning system provides precise position information for the transducer carriage along the arc guide assembly which, in turn, allows for a precise and accurate ultrasonic scan to be made. FIG. 6 shows a scan head mounted on a scan head positioning assembly described previously. The scan head comprises an arc guide assembly 602 and a transducer carriage assembly 601. Transducer 603 has been described previously. An OTS magnetic encoder (such as for example a Siko MSK5000) is contained in a housing 604 mounted on the side of the transducer carriage assembly 602. The magnetic encoder senses its position by reading a magnetic strip 605 (shown as a black strip underneath the housing 604) which is attached to the arc guide track. The magnetic strip 605 is a flexible magnetic material with alternating north/south poles and with a distance between poles known to the encoder. The encoder then outputs standard quadrature encoder pulses as it moves along the magnetic strip. This model of encoder with the recommended magnetic strip delivers a 1 micron resolution or about 0.0005 degrees at the radius of the arc scanner.

The magnetic positioning system is based on a home position on the arc guide track for the arc carriage and a series of magnetic combs installed along the arc guide track and whose spacings are accurately known. A coil in the arc carriage then counts current pulses as the carriage passes over the magnetic combs to determine a precise position of the carriage along the arc guide track. Other position sensing systems are possible. These include optical systems (optical bars replace the magnetic combs), mechanical systems and electrical systems (such as a potentiometer). The magnetic sensing system is preferred over the optical system which requires periodic cleaning and the mechanical system which is subject to buildup of mineral and other deposits.

Fluidic Bearing

A bearing mechanism is another component of an arc scanner. The function of the bearing is to allow smooth motion of the transducer assembly along the arc guide assembly which has been positioned by a scan head positioning apparatus such as described above in FIGS. 4 and 5. A successful scan normally requires that the transducer assembly move smoothly and without jitter or jerk along the curved arc guide assembly to take advantage of the precision of a high frequency ultrasonic pulse (in physics, jerk is the rate of change of acceleration; more precisely, the derivative of acceleration with respect to time, the second derivative of velocity, or the third derivative of displacement).

The carriage has a set of liquid passages that communicate with a source of liquid under pressure. The liquid passages also communicate with ports located on the smoothly conforming aspect of the carriage that meets a matching surface on the arc guide track to form a fluidic bearing. The liquid flows from the source through the passages to and through the ports, forming a liquid film between the carriage and the arc guide track. The pressure from the ports and in the liquid film urges or forces the carriage and the arc guide track apart, causing them to separate, reaching an equilibrium position with a thin film of liquid flowing out from between them. Following known practice in fluidic bearings, the size of the passages is chosen to make the pressure at each port largely independent of the flow through the other ports to provide stability to the fluidic bearing. It is preferred that the passages and exit ports are in the transducer carriage rather than in the arc guide track so that the ports are always covered, an arrangement that reduces the liquid mass flow requirement.

As will be described below, a linear motor is used to propel the transducer carriage along the arc guide. The permanent magnets in the transducer carriage attract the carriage to the arc guide with considerable force. This makes it possible to use a fluidic bearing system as the fluid pressure generated force can be made to approximately balance the magnetic attraction force. This minimizes any mechanical drag of the transducer carriage on the arc guide and allows the system to move smoothly and without jitter.

Figure 7:
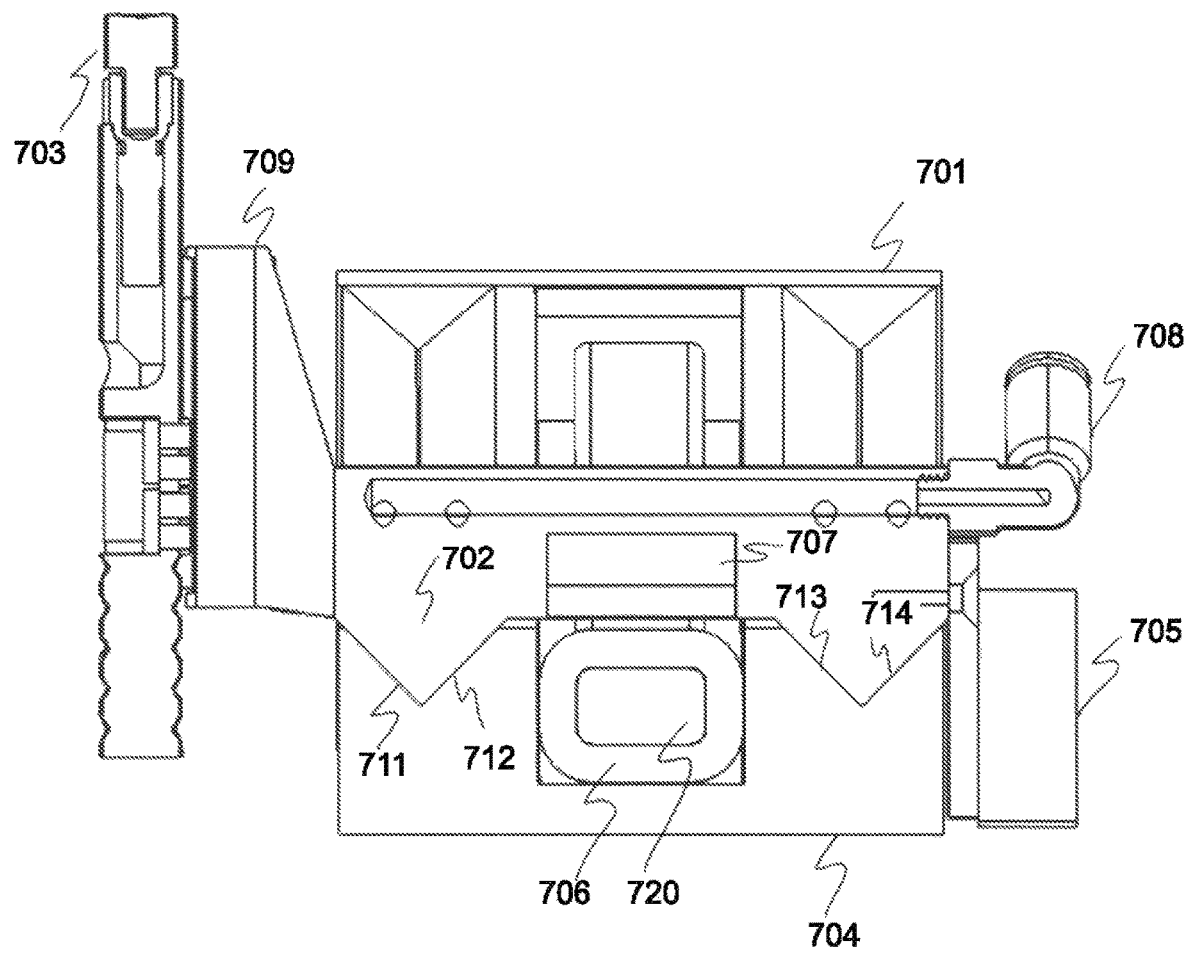
FIG. 7 illustrates a fluidic bearing operative between a fixed arc assembly and a moving transducer assembly.

FIG. 7 illustrates a fluidic bearing operative between a fixed arc guide assembly 704 and a moving transducer carriage assembly 702. It is understood that once the arc guide assembly 704 has been moved into position and secured by the positioning mechanism described in FIGS. 4 and 5, the motion of the transducer carriage assembly 702 is constrained to be along the arc guide assembly 704 for subsequent scanning operations. The view shown in FIG. 7 is a normal section through the arc guide assembly 704 and a moving transducer carriage assembly 702, with the rest 701 of the arc guide assembly 704 curving upward in the background. The arc guide assembly 704 contains linear motor coil elements 706 and their iron cores 720 which will be described further in FIGS. 8 and 9. The moving transducer carriage assembly 702 includes an ultrasonic transducer 703, a transducer mount 709 and a magnetic sensor housing 705. A water hose (not shown) is connected via fluid coupling 708. An electrical conduit that transmits electronic signals to and from the transducer and transmits electronic signals to and from a position sensing means is not shown but is also attached to the transducer carriage assembly 702. The position sensing means for determining the relative position between the moving transducer carriage assembly 702 and the arc guide assembly 704 may be, for example, a magnetically coded strip along the arc guide assembly 704 and a magnetic sensing element on the moving transducer carriage assembly 702, such as described in FIG. 6.

The ability to accurately detect the relative position between the moving transducer carriage assembly 702 and the arc guide assembly 704 can be important because it can accommodate non-uniform motion of the moving transducer carriage assembly 702. For example, the transducer carriage assembly 702 may accelerate from rest at one end of the arc guide, reach a maximum velocity which may be maintained briefly near the center of the arc guide and then decelerate to rest at the opposite end of the arc guide. As a result of knowing the transducer carriage assembly 702 position along the arc guide, the pulsing and receiving periods of the transducer 703 can be programmed to correlate with the motion the transducer 703 along the arc guide so that a coherent image may be formed. The ability to operate with a non-uniform transducer carriage assembly 702 motion is enabled by the smooth acceleration and deceleration allowed by the fluidic bearing. FIG. 7 shows the bearing surfaces 711, 712, 713 and 714 between the arc guide assembly 704 and the moving transducer carriage assembly 702.

Since the entire arc scan head assembly is under water, it is natural to use a fluid bearing where the fluid is also water. The fluid is pressurized by a small pump mounted on the transducer carriage assembly 702 and water is pumped through small holes located at regular intervals along the bearing surfaces 713 and 714 of the transducer carriage assembly 702. The water in the main arc scan head chamber is commonly at approximately 1 bar or ambient pressure. The pump delivers fluid at pressures typically in the range of ½ to 2 bars above ambient pressure. The pressurized fluid then lifts the transducer carriage assembly 702 about 5 to about 10 microns off the surface of the arc guide assembly 704 and maintains this separation while fluid is continuously pumped through the small holes located along the bearing surfaces 713 and 714 of the transducer carriage assembly 702.

As has been shown experimentally, the linear motor cannot move the transducer carriage assembly 702 until the fluid bearing is activated because of the strong attractive force between magnets 707 and iron cores 720. Once the fluid is being pumped through the small holes located along the bearing surfaces 713 and 714 of the transducer carriage assembly 702, the transducer carriage assembly 702 rises to achieve a separation of a few microns and moves freely and without jerk along the arc guide track.

Linear Motor

The function of the motor is to move a transducer carriage assembly along an arc guide assembly so as to allow an ultrasonic scan of an eye component to be made. The linear motor must be able to be operated safely under water since the entire arc scanning head is immersed in water.

The following descriptions assume that the linear motor has magnets in the carriage and windings in the circular track. It should be noted that this could have been reversed, with the magnets in the circular track and the windings in the carriage, without changing the fundamental operation of the scanning system. Placing the magnets in the carriage represents the preferred embodiment and the best mode known to the inventors.

The transducer carriage has one or more magnets affixed to it, and the track is made of or contains magnetic material such as iron. The magnets are arranged in the carriage so that the resulting magnetic field urges or attracts the carriage toward the track. Because the entire track and the carriage must be submerged in water during normal operation, the magnetic components are protected from corrosion by either choosing the exposed iron material to be a magnetic stainless steel or by sealing the iron in a material such as epoxy to protect it from water exposure.

The transducer carriage assembly typically weighs in the range of about 0.1 kg to about 0.3 kg. This range of carriage assembly mass is light enough to allow rapid acceleration and deceleration yet heavy enough to provide sufficient inertia to filter out extraneous mechanical jitter in the motion of the transducer carriage along the arc guide track. The location of the center of mass of the transducer carriage is also important as it is desired that the carriage be reasonably balanced on the guide track.

Figure 8:
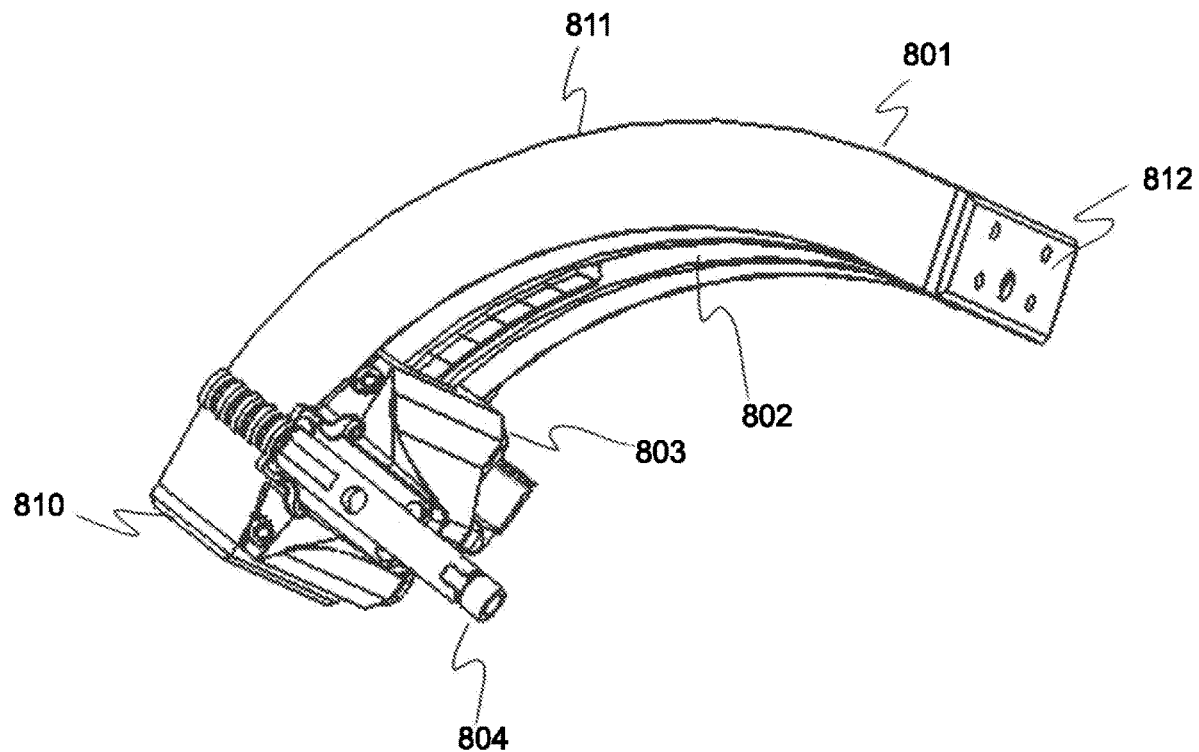
FIG. 8 is an isometric schematic of a linear induction motor to move a transducer assembly along a fixed arc assembly.

FIG. 8 is an isometric schematic of an apparatus containing a linear induction motor to move a transducer carriage assembly 803 along an arc guide assembly 801. FIG. 8 shows a transducer assembly 803 with an ultrasonic transducer 804. The ultrasonic transducer 804 is mounted such that it always points at the center of curvature of the arc defined by the radius of curvature of arc guide assembly 801. The transducer carriage assembly 803 moves along an arc guide assembly 801, propelled by a linear induction motor arrangement. The motion of the transducer carriage assembly 803 may be non-uniform. For example, the transducer assembly 803 may accelerate from rest at one end 810 of the arc guide assembly 801, reach a maximum velocity which may be maintained briefly near the center 811 of the arc guide assembly 801 and then decelerate to rest at the opposite end 812 of the arc guide assembly 801. In a preferred embodiment, permanent magnets are installed in the transducer carriage assembly 803 and electrically powered field coils are installed down a central groove formed in the in the fixed arc assembly 801. An example of such a groove and field coils can be seen in FIG. 7 with field coils 706 positioned in a groove in the arc guide assembly 704.

Figure 9:
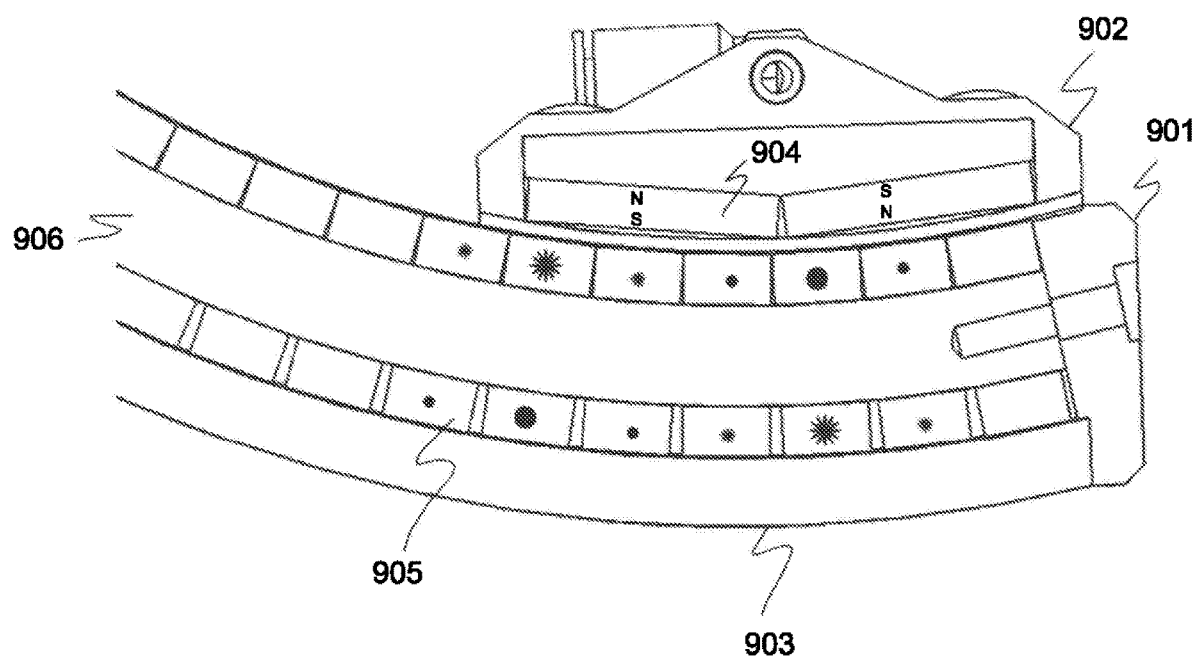
FIG. 9 shows a schematic of the currents and magnetic forces that propel a transducer carriage along an arc guide track.

FIG. 9 shows a schematic of the currents and magnetic forces that propel a transducer carriage along an arc guide assembly 903. A transducer carriage 902 is shown with two permanent magnets 904 mounted side-by-side but with their north-south polarities on opposite faces. The two permanent magnets 904 are preferably of equal size. A carriage track 903 which forms an arc is shown with several wound conductive coils 905, wound around an iron core 906 which is also formed as an arc in this side view. The coils 905 are approximately rectangular in cross section as shown, for example, in FIG. 7 by callout 706. The long side of the rectangular coil windings is preferably adjacent to the face of the magnets to maximize propelling force (this force is described below). The coils 905 may be made of any conductor material such, as for example, copper, aluminum and the like. The coils 905 are preferably sized and spaced such that three adjacent coils are approximately the same width as either one of the permanent magnets 904. Starting at either end 901 of the arc guide, each set of three adjacent coils is powered by a 3 phase electrical circuit. The 3 phase circuit voltages are controlled by a Pulse Width Modulated (PWM) system that is in turn controlled by the position of the transducer carriage 902. The position of the transducer carriage 902 relative to the arc guide 903 is determined, for example, by a magnetic strip sensor system such as described in FIG. 6. The combination of PWM; an accurate location sensing system; a fluid bearing between the arc guide and the transducer carriage (described in FIG. 7); and the mass of the transducer carriage provides a very smooth motion of the transducer carriage 902 which is essential to making sharp, precision high-frequency acoustic measurements (approximately 3 MHz to approximately 60 MHz).

In this application, it is preferable to embed the permanent magnets 904 in the moving transducer carriage 902 and to embed the coils 905 in the arc guide assembly 903. Embedding the permanent magnets 904 in the moving transducer carriage 902 adds mass to the transducer carriage assembly 902 which helps to keep its motion along the arc guide track smooth. Embedding the coils 905 in the arc guide assembly 903 reduces the motion in the water of the electrical wires connecting the power source with the coils since the motion from positioning the scan head is far less than the motion of the transducer carriage back and forth along the arc guide track. This is a slightly less energy efficient design for a linear motor since all the coils are energized by the 3 phase power supply. However, motor efficiency is not a major concern in this application.

With the transducer carriage position shown in the example of FIG. 9, the gap between the permanent magnets 904 is lined up with the gap between two adjacent coils 905 such that three coils 905 are centered beneath each permanent magnet 904. The current is at a maximum in the two coils centered beneath each permanent magnet but in opposing directions as indicated by the current arrows represented by an end view of an arrow feather and an end view of an arrow head. The current is low but in the same direction in the coils adjacent to the coils carrying the maximum current, as indicated by the smaller current arrows. In this position, there is a force exerted on each of the magnets 904 along the same direction of the arc 903. Since the magnets 904 are embedded and attached to the transducer carriage 902, the transducer carriage 902 is propelled along the arc guide assembly.

In this example, the coils 905 are wound around an iron core which is approximately rectangular in shape (although with rounded corners so as not to cut the coil wire as shown for example in FIG. 7 by callout 706). The propelling force arises from the current in the coil elements adjacent to the permanent magnets interacting with the local magnetic field of the permanent magnets according to the well-known equation:

$$dF = I\, dl \times B$$

where dF is the differential force

I is the total current (number of windings times current in each winding)

dl is a differential length of coil winding

X represents the cross-product between dl and B and B is the local magnetic field of the permanent magnet As can be seen, the force is orthogonal to both the direction of the current and the direction of the local B-field and so the force on the permanent magnets is along the arc guide assembly. It is noted that the force is caused by the current in the coil winding elements adjacent to the permanent magnet. The force caused by the current in the coil winding elements distant from the permanent magnet is in the opposite direction but is very weak as it is effectively shielded by the iron core 906. The force caused by the current in the coil winding elements normal to the arc track are largely parallel to the magnetic field of the permanent magnets and so do not contribute to the propulsive force on the transducer carriage 902.

The permanent magnets 904 are held in place with a back iron component whose face is flush with the pole faces of the permanent magnets. The back iron with the two permanent magnets 904 thus form, in essence, a horseshoe magnet and can in fact be replaced by an appropriately shaped horseshoe magnet. A magnetic circuit is thus formed by the back iron, the permanent magnets 904 and the iron core 906.

Eyepiece

An eyepiece serves to complete a continuous acoustic path for ultrasonic scanning, that path extending from the transducer to the surface of the patient's eye. The eyepiece also separates the water in which the patient's eye is immersed from the water in the chamber in which the arc track assembly are contained. Finally, the eyepiece provides a steady rest for the patient and helps the patient to remain steady during a scan. To be practical, the eyepiece should be free from frequent leakage problems, should be comfortable to the patient and its manufacturing cost should be low since it should be replaced for every new patient.

Figure 10:
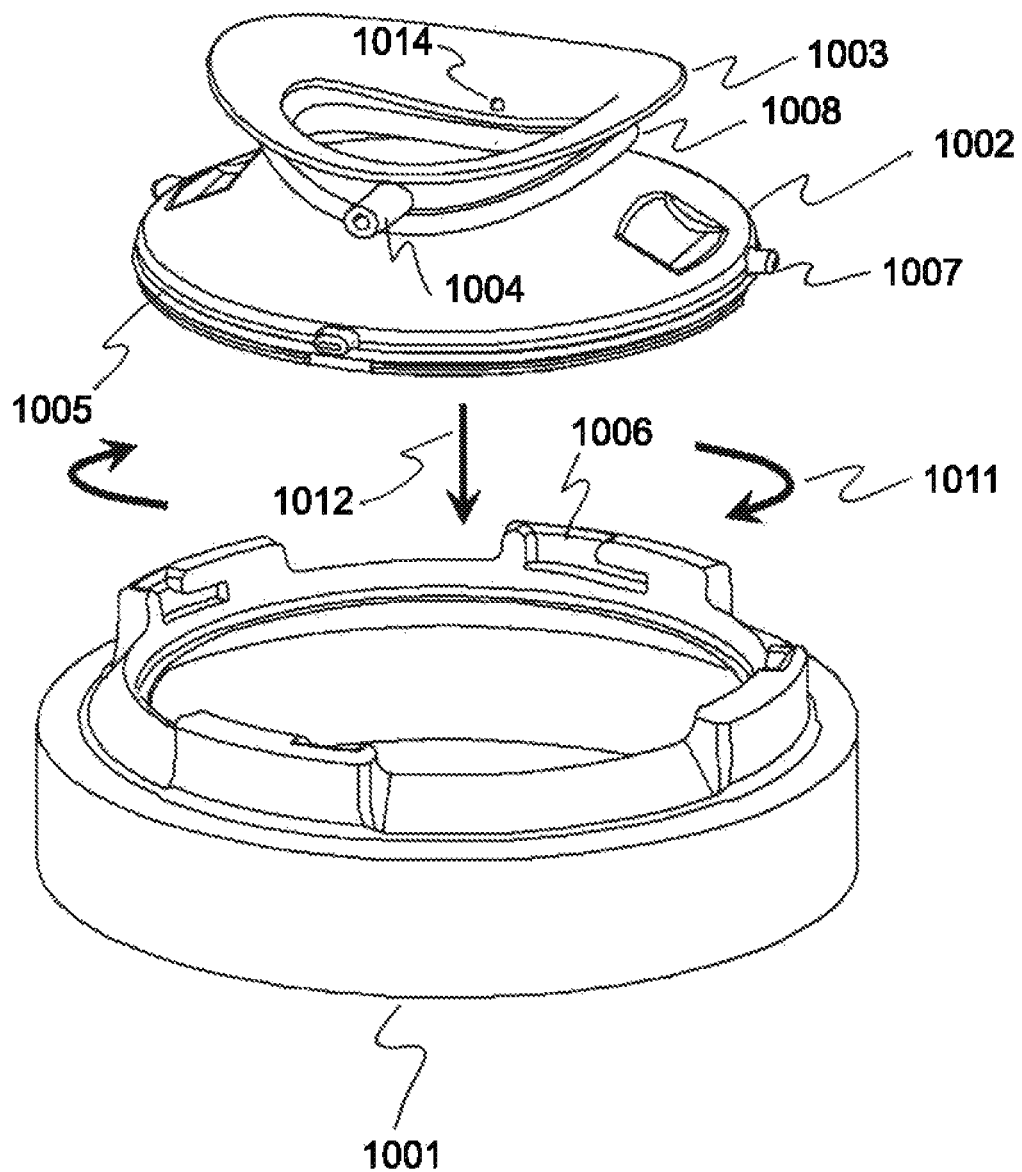
FIG. 10 illustrates an embodiment of an eyepiece for an arc scanner.

FIG. 10 illustrates an embodiment of an eyepiece that satisfies these requirements. The eyepiece comprises a mounting ring 1001 and an eye seal ring 1002. The mounting ring 1001 is attached to and is typically a permanent part of the main arc scanner assembly. As shown here the mounting ring 1001 has several attachment grooves 1006 which can accept attaching mechanisms 1007 on an edge 1005 of the eye seal ring 1002. In this embodiment, the attaching mechanisms 1007 are pushed down 1012 into the attachment grooves 1006 and then rotated 1011 into position to form a mechanical connection that seals the eye seal ring 1002 against the mounting ring 1001 to prevent water leakage. This is also known as a bayonet type connection. There may be a sealing ring 1005 which is compressed as the attaching mechanisms 1007 are rotated 1011 into position. The eye seal ring 1002 has a soft rubber or foam contoured face seal 1003 which is designed to seal against a typical human face around the eye that is to be scanned. The eye seal ring 1002 is also shown with its water fill tube 1004 on the top and a water drain tube 1014 on the bottom. A sealed hygienic barrier (not shown) is formed as part of the eye seal ring 1002 during manufacture and is typically located where the contoured face seal 1003 is connected at location 1008 to the main body of the eye seal ring 1002.

The hygienic barrier or membrane may be permeable or semi-permeable to water as long as it is impermeable to bacteria, viruses, fungi, and other potentially harmful biological and chemical impurities. The membrane is preferably impermeable to water to provide superior isolation from biological and non-biological impurities that may be dissolved or carried in water. The membrane is preferably optically clear to allow a video camera to view the eye (see FIG. 3) through the membrane. The membrane preferably passes acoustic pulses without significant energy absorption or reflection. These conditions can be substantially met by a membrane that is thinner than an acoustic pulse wavelength. Eyepiece membranes have been made from materials such as, for example, polyethylene, mylar, polypropylene; vinylidene chloride; polyvinylidene chloride; or DuraSeal (made by Diversified Biotech) which is polyethylene based and free of and adhesives. A preferred material is medical grade polyethylene which has an acoustic impedance only somewhat higher than that of water (about 2.33 million $kg/m^2$-s compared to 1.54 million $kg/m^2$-s for water). The thickness of the membrane is preferably in the range of about 10 to about 30 microns. This thickness is a small part of an acoustic wavelength in water which is about 150 microns at 10 MHz and about 20 microns at 80 MHz.

Figure 11:
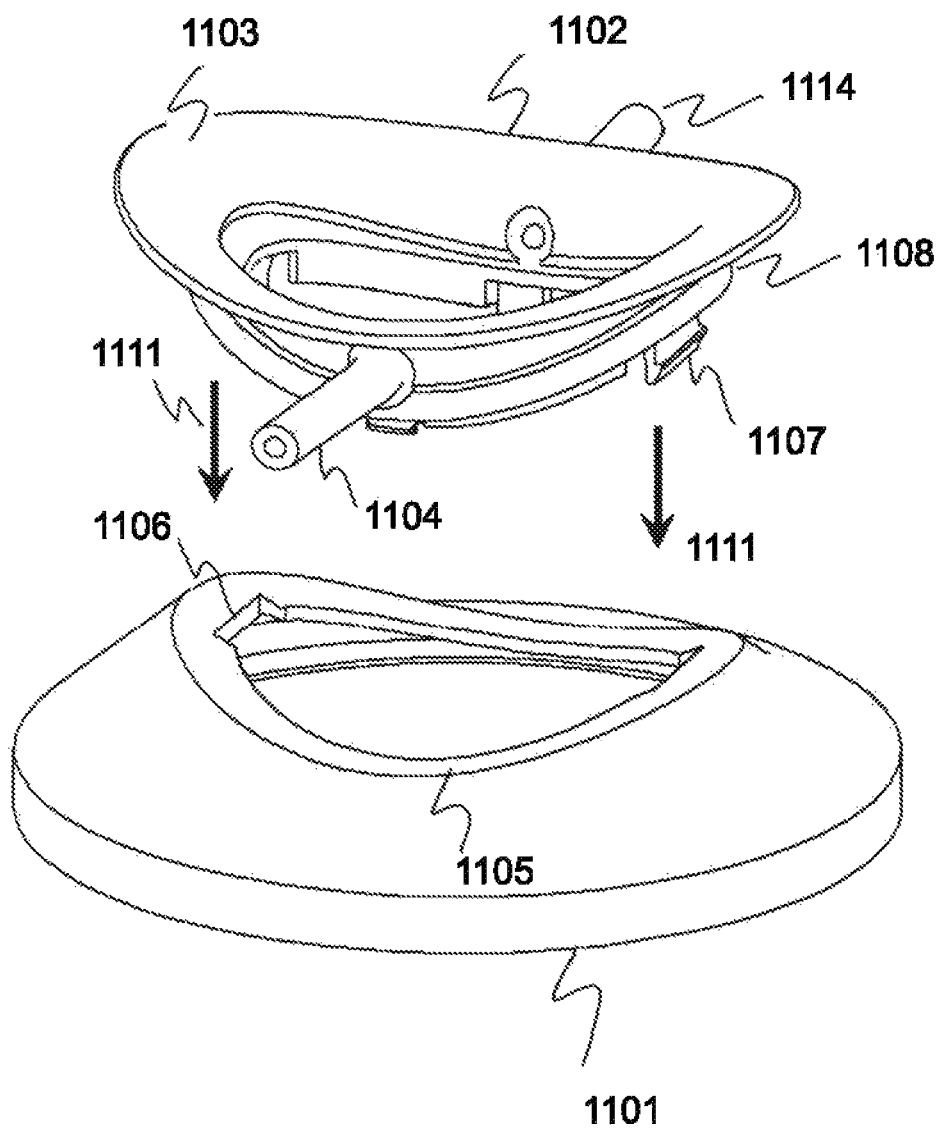
FIG. 11 illustrates an alternate embodiment of an eyepiece for an arc scanner.

FIG. 11 illustrates an alternate embodiment of an eyepiece that also satisfies the practical requirements described above. The eyepiece comprises a mounting ring 1101 and an eye seal ring 1102. The mounting ring 1101 is attached to and is typically a permanent part of the main arc scanner assembly. As shown here the mounting ring 1101 it has several attachment grooves 1106 which can accept attaching mechanisms 1107 on an edge 1108 of the eye seal ring 1102. In this embodiment, the attaching mechanisms 1107 are pushed down 1111 into the attachment grooves 1106 and then snapped into position to form a mechanical connection that seals the eye seal ring 1102 against the mounting ring 1101 to prevent water leakage. This is also known as a snap-on type connection. There may be a sealing surface 1105 on the mounting ring 1101 and a matching sealing surface (not shown) on the eye seal ring 1102 which is compressed when the attaching mechanisms 1107 are snapped into position. The eye seal ring 1102 has a soft rubber or foam contoured face seal 1103 which is designed to seal against a typical human face around the eye that is to be scanned. The eye seal ring 1102 is also shown with its water fill tube 1104 on the top and a water drain tube 1114 on the bottom. A sealed hygienic barrier (not shown) is formed as part of the eye seal ring 1102 during manufacture and is typically located where the contoured face seal 1103 is connected at location 1108 to the main body of the eye seal ring 1102.

Figure 12:
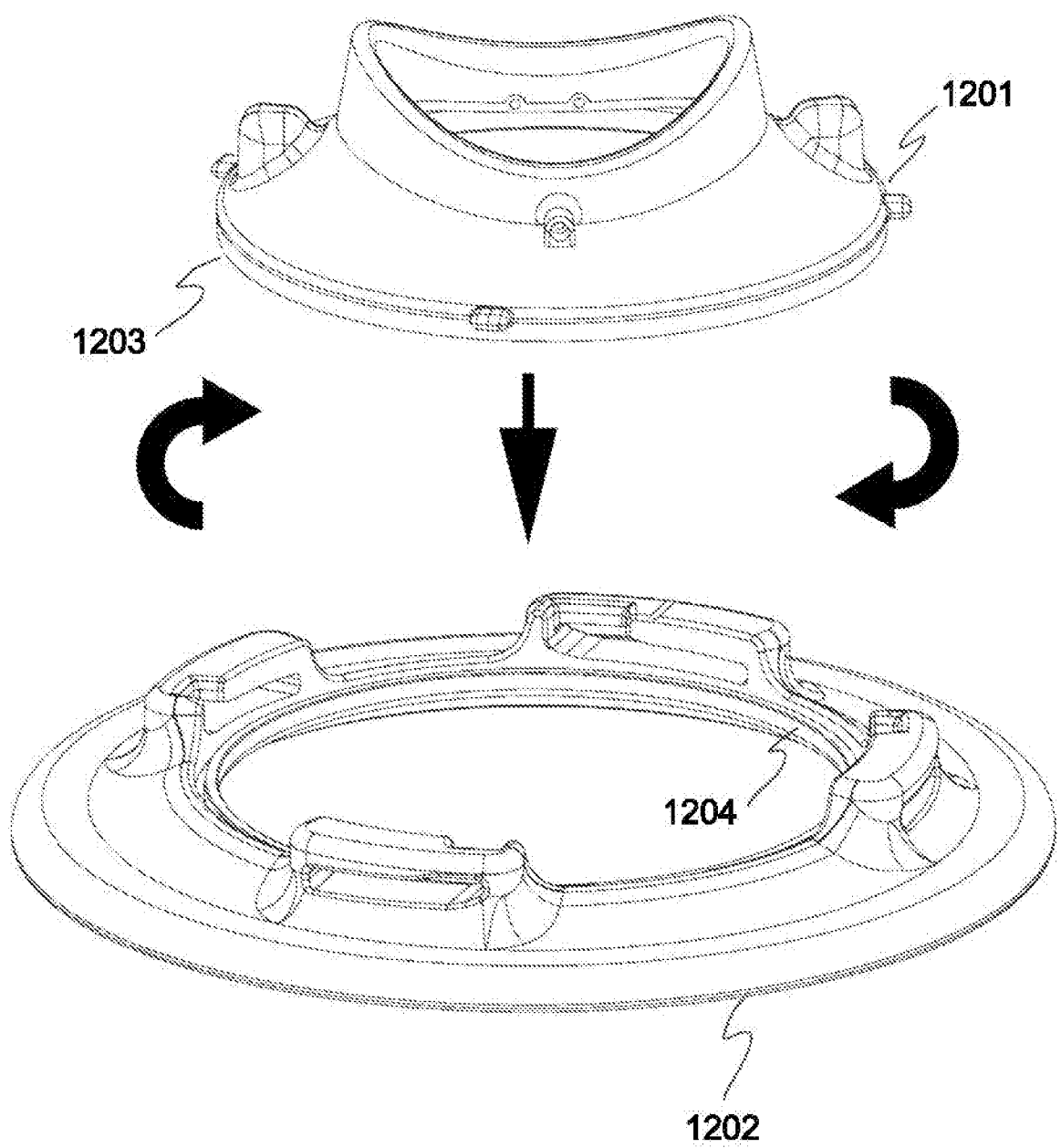
FIG. 12 illustrates another alternate embodiment of an eyepiece for an arc scanner.

FIG. 12 illustrates yet another an embodiment of an eyepiece for an arc scanner. The eyepiece comprises a mounting ring 1202 and an eye seal ring 1201. The mounting ring 1202 is attached to and is typically a permanent part of the main arc scanner assembly. As shown here the mounting ring 1202 has several attachment grooves, such as described in FIG. 10, which can accept attaching mechanisms on the eye seal ring 1201. In this embodiment, the attaching mechanisms are pushed down into the attachment grooves and then rotated into position, such as described in FIG. 10, to form a mechanical connection that seals the eye seal ring against the mounting ring to prevent water leakage. This is also known as a bayonet type connection. In the embodiment disclosed in FIG. 12, there is an additional sealing feature comprises a groove 1203 molded as part of the eye seal ring 1201 and a matching tongue 1204 molded as part of the mounting ring 1202. When the eye seal ring 1201 is rotated into position with the mounting ring 1202, the tongue and groove form a threaded connection as described in FIG. 13 which compress as the parts are rotated into position. This is similar in sealing action to a plastic bottle with a threaded top. Since both the eye seal ring 1201 and the mounting ring 1202 are typically made from a plastic, the compliance of the plastic further helps in forming a water tight seal. The eye seal ring 1201 has a soft rubber or foam face seal (not shown here) which is designed to seal against a typical human face around the eye that is to be scanned. A sealed hygienic barrier (not shown) is formed as part of the eye seal ring 1201 and is typically located where the contoured face seal is connected to the main body of the eye seal ring 1201.

Figure 13A:
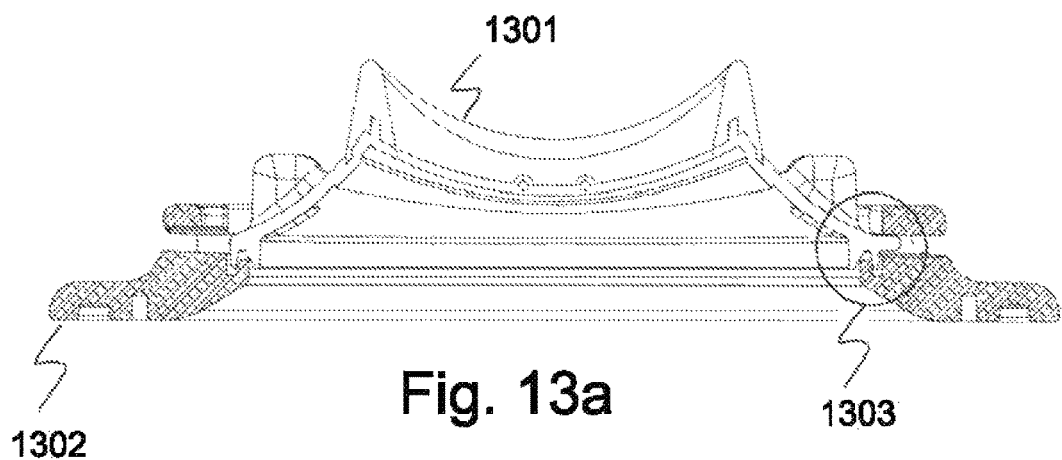
FIG. 13a illustrates the sealing method for the eyepiece of FIG. 12.

FIG. 13 shows a section side view illustrating the tongue and groove portion of the sealing method for the eyepiece of FIG. 12. FIG. 13*a* shows an eyepiece comprising a mounting ring 1302 and an eye seal ring 1301 is shown in sectional view with its tongue and groove sealing system indicated by callout 1303.

Figure 13B:
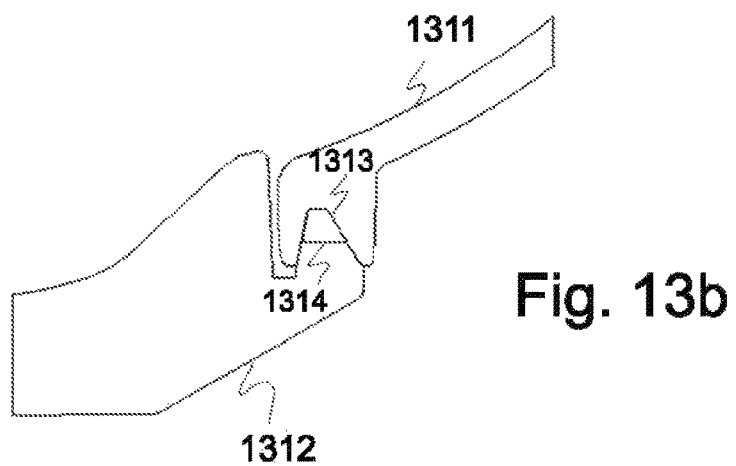

FIG. 13*b* illustrates a close up view of tongue and groove portion of the sealing method for the eyepiece of FIG. 13*a*. The eyepiece mounting ring 1312 has a tongue 1314 molded into the eyepiece mounting ring 1312. The eye seal ring 1311 has a matching groove 1313 molded into the eye seal ring 1311. When the eye seal ring 1311 is rotated into position with the mounting ring 1312, the tongue 1314 and groove 1313 compress, deform as necessary and form a tight seal as the parts are rotated into position.

As described previously, the eye seal ring typically includes a soft rubber or foam contoured face seal which is designed to seal against a typical human face around the eye that is to be scanned. The contoured face seal may also be made from a foam material impregnated with, for example, mineral oil, to provide a superior sealing action against a typical human face around the eye. An alternative face sealing mechanism can also be provided by a hollow soft rubber or soft plastic ring molded into the removable eye seal ring that can be filled with water after the patient has placed their face against the eyepiece. This would be a third separate water-filled component of an arc scanner and would serve to better seal against the face around the eye for patients with irregular facial features around the eye.

Precision Ultrasound Scanning for Other Body Parts

The current disclosure is also directed towards an imaging system that provides the convenience and lower cost of ultrasound imaging systems but with both high penetration depths and excellent resolution. This is achieved through a combination of ultrasound technologies and methods for holding and stabilizing the ultrasound probe relative to the body surface and the body part to be imaged.

A conforming body seal and portable instrument body are disclosed, that together provide for a compact yet stable fixation of the probe relative to the body surface as compared to currently available handheld ultrasound systems. This enables longer scan times to be achieved because of the elimination of probe movement relative to the body part during a scan. Ultrasound imaging techniques such as coded excitation (chirp excitation in its simplest form), oversampling/averaging and dynamic focal plane imaging can be utilized allowing much higher operating frequencies (frequencies in a range of about 20 MHz to about 80 MHz) with their higher resolution and yet approaching penetration depths of traditional low frequency (about 5 MHz to about 10 MHz) ultrasound handheld systems.

This arrangement includes computer controlled movement of the ultrasound probe providing multiple image cross-sections for 3D imaging of targeted tissue or selection of a particular cross-section from a set that best isolates the tissue of interest without having to reposition the system by hand multiple times. This arrangement provides much higher repeatability of image biometry due to repeatable fixation of the probe relative to the body surface.

Portable Ultrasound Scanner

Figure 14:
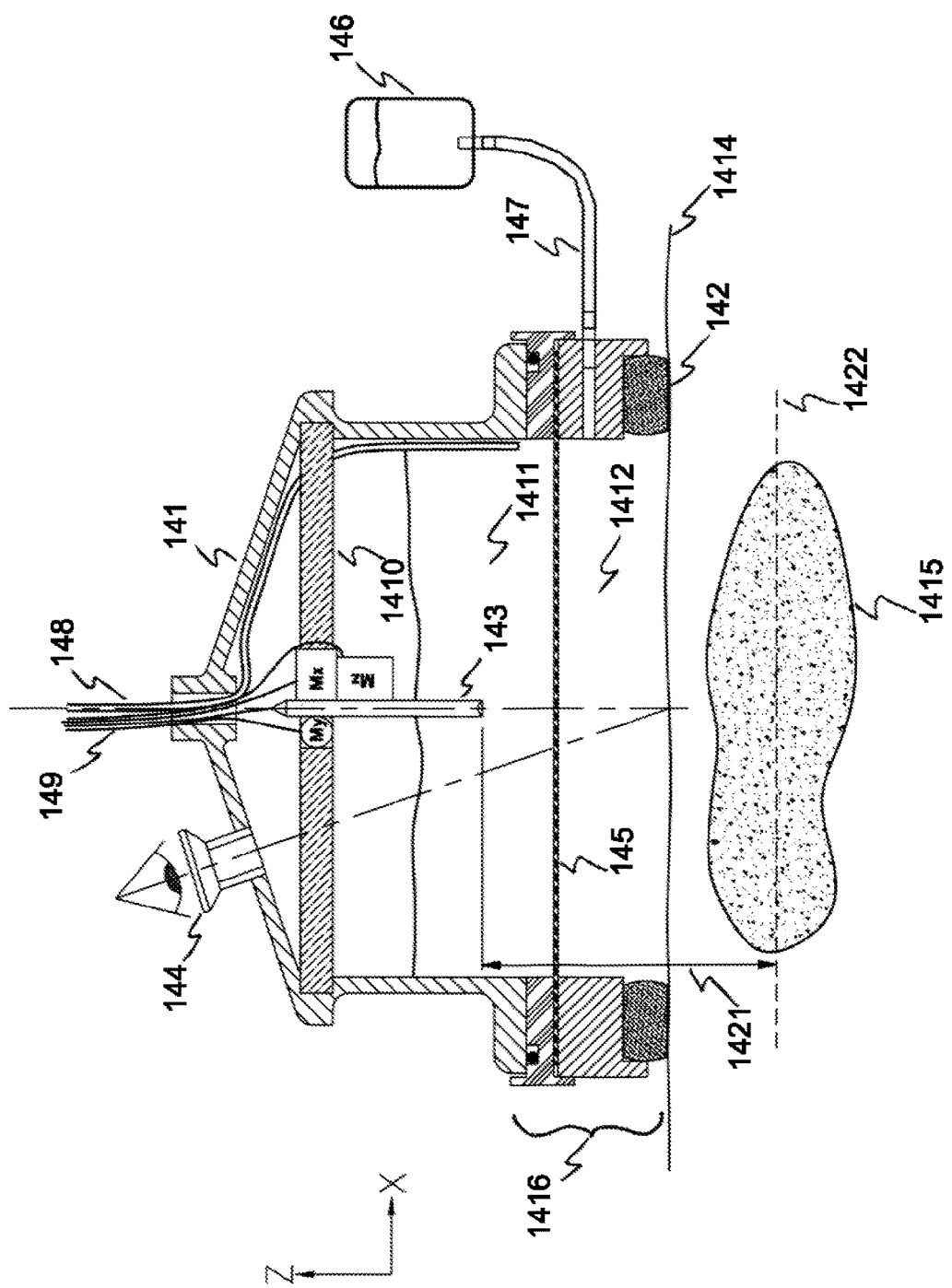
FIG. 14 is a side view of an ultrasound scanner system with a single element ultrasound transducer.

FIG. 14 is a side view illustrating the basic components of an ultrasound scanner system with an ultrasound probe comprised of a single element ultrasound transducer. The device is comprised of a housing assembly 141 which is pressed to the surface layer 1414 of the patient overlaying the body part of interest 1415 and sealed by a conforming seal 142 to minimize leakage of saline solution 1412. A membrane 145 separates the saline solution 1412 from the water 1411 used to immerse the ultrasound probe 143. This membrane prevents water used in the probe section of the housing from mixing with the saline solution used in the section of the housing in contact with the patient.

Assembly 1416 which holds membrane 145 in place is comprised of a clamp, sealing system and a conforming seal 142. Conforming seal 142 may also be comprised of a layer of adhesive to facilitate the seal adhering to the patient's skin 1414. Assembly 1416 corresponds in function to the disposable eyepiece used in an ultrasound eye scanner such as described in a previous section of this disclosure. The entire assembly 1416 is may be a disposable item that can be readily changed for each new patient.

As can be appreciated, the saline solution may or may not be a sterile saline solution depending on the body part to be scanned. If the body part to be scanned is covered by intact skin then the saline solution need not be sterile and may be replaced with distilled water. In some cases, only the conforming seal may be replaced for scanning other body parts. In general, the entire assembly 1416 is replaced for each new patient. When the body part is an eye or when the body part is covered by injured or damaged skin, then a sterile saline solution should be used and the entire assembly should be replaced for each new patient.

Both the saline solution 1412 and water bath 1411 are at ambient pressure, typically 1 atmosphere. In operation, the assembly is first placed over the body part of interest. Then the instrument chamber in the upper part of the housing is filled with water (typically distilled water) via fill tube 148, fully immersing the ultrasound probe 143. Then the saline solution 1412 is introduced via fill tube 147 into the sealing chamber that connects a disposable saline fill bag 146. The operator can view the region around surface layer 1414 overlaying the body part of interest 1415 through positioning eyepiece 144. The motion of the ultrasound probe 143 is controlled in three orthogonal directions x, y and z by motors Mx, My and Mz. The computerized operating instructions for these motors and the ultrasound probe 145 are communicated through cable bundle 149. Motors Mx, My and Mz are operated under computer control to move the probe up and down in the z-direction or back and forth in the x- and y-directions on linear positioning assembly 1410. The nominal focal distance of the ultrasound transducer 1421 is typically set as the distance from the pulse emitting element located at the tip of ultrasound probe 143 to approximately the centerline 1422 of the body part of interest 1415. The ultrasound probe may be comprised of a single pulse emitting and receiving element or a more complex probe embodiment such as described in FIGS. 16 and 17. If an ultrasound probe comprised of a single pulse emitting and receiving element is used, the center pulse frequency is typically in the range of about 5 MHz to about 80 MHz. The depth of field of a single frequency focused probe is typically about 1 to 2 millimeters at about 40 MHz and a focal distance of about 12 millimeters.

Figure 15:
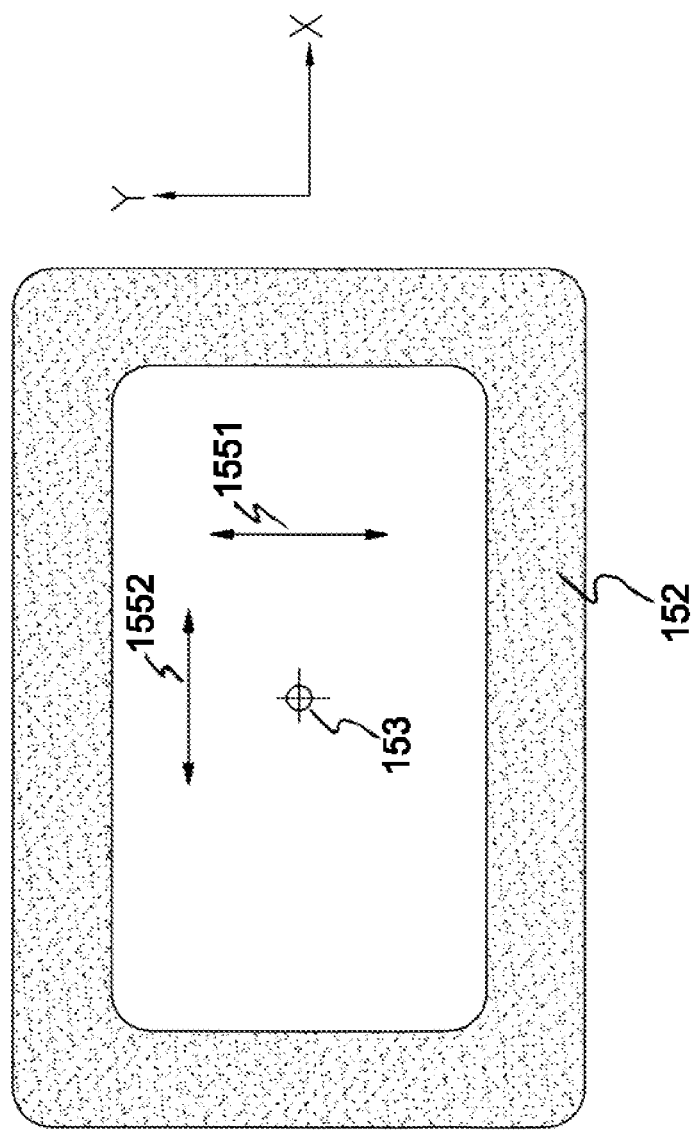
FIG. 15 is a top view of an ultrasound scanner system.

FIG. 15 is a top view of an ultrasound scanner system. This view shows the "footprint" of the conforming seal 152. Ultrasound probe tip 153 can move in the x-direction 1552 and/or in the y-direction 1551 by using the linear positioning assembly 1410 described in FIG. 14.

An example of a linear positioning assembly is disclosed in U.S. Pat. No. 8,317,702, entitled ""Alignment and Imaging of An Eye with an Ultrasonic Scanner" which is incorporated herein by reference.

Description of Components

Disposable Conforming Body Seal

Referring again to FIG. 14, the disposable body seal 1416 is a component that may come in different shapes and forms to allow for optimal fit to a variety of body surfaces. It may have a shape to fit around the eye socket, be more curved to fit around a particular joint, or be more gently curved to fit on a more planar body surface such as an abdomen or back. All the sub-components described below are attached to one another into a single assembly 1416.

A first sub-component is a conforming seal 142 of a low durometer plastic or foam which easily conforms to the body surface and outlines the entire area to be scanned. This seal is designed to adhere on the body side to the skin surface to provide a stable fixation of the system to the body and provide a seal of the sterile saline solution 1412.

A second sub-component is a lower ring which provides for a rigid backing for the conforming seal and fill and drain lines 147 for the saline fill.

A third sub-component is a membrane 145 that separates the disposable saline fill from the instrument system fluid (which is typically distilled water and is filtered and may be reuseable). This membrane 145 must be acoustically transparent (that is, it must have an acoustic impedance similar to that of water) to the ultrasound beam and optically transparent to allow manual positioning of the system to the healthcare provider's mark on the body surface. This membrane is bonded to both the upper and lower rings and provides a fluid seal for both the handheld fluid on one side and the sterile saline solution on the other.

A fourth sub-component is an upper ring which provides for mechanical coupling of the body seal to the portable body and sealing of the fluid by O-ring or other suitable sealing method.

A fifth sub-component is a saline fill bag 146 and lines 147 which provide the single use sterile saline fill fluid. Fill control can be, for example, by squeezing the fill bag 146 by hand to force saline fluid into the volume between the membrane and body surface and out again through an overfill line.

Instrument Main Body

The portable instrument main body 141 is a component that serves as the main frame of the system and serves as the mounting of several system components including the disposable body seal on the bottom of the instrument. The system components housed in the instrument main body include the positioner carriage (described below).

The portable instrument main body is comprised of a sealed chamber to contain the fluid (called the instrument chamber), typically distilled water, around the ultrasound probe. The system also includes fluid management system (not shown) which provides for filling and draining of the fluid 1411 to/from the instrument chamber and for the fluids storage and maintenance. The system instrument main body also includes a feed-through to provide for a means to get the electrical signals to and from the ultrasound probe and the positioner motors and sensors, which are inside the instrument chamber, to an external pulser, motion control, signal/image processing and display system (described below). If the device is an eye scanner, then a fixation target is included which provides a means for aligning the visual axis of the eye to the ultrasound axis as disclosed in U.S. Pat. No. 8,496,588, entitled "Procedures for an Ultrasonic Arc Scanning Apparatus" which is incorporated herein by reference.

The system also includes a positioning eyepiece (described below) and a means for strapping the handheld instrument (not shown) around the limb or torso or head as a backup to the body seal disposable to assist in the stabilization of the handheld instrument to the body surface.

Positioner Carriage

The positioner assembly 1410 is a subsystem that provides for fixating the ultrasound probe to a single or multi-axis movement system (including its actuators such as stepper motors) which is in turn are mounted inside the sealed chamber of the instrument main body.

The movement system can be a single axis in its simplest form providing an image with only a single cross-section of the object to scan. The movement system could provide 2 or 3 axes of movement. In the system shown in FIG. 14, two linear axes of movement are shown in the x- and y-directions. This would provide for a multitude of cross-sections of an object with the possibility of providing 3D images. A third linear z-axis movement is shown for additional control of the depth of the optimal image for relatively deeper or shallower objects.

A movement axis could also be arcuate to better conform to the tissue to be imaged such as the cornea (as in the case of an eye scanner) or for a bending joint such as a knee or elbow.

Positioning Eyepiece

The positioning eyepiece 144 is a simple, low power optical microscope allowing the operator to center the position of the instrument on a mark on the body surface placed prior to mounting of the instrument by the healthcare professional or in the case of the eye scanner centering on the iris of the eye. This insures the image will capture the selected body part. In the case of two or more positioning axes, this positioning need only be approximate as the scan area will be sufficient to allow complete capture of the object body part even if not perfectly centered on the object body part. In the case of the eye scanner, additionally a reflection of a fixation target will be centered through the eyepiece for precision alignment of the positioner carriage.

Ultrasound Probe

An ultrasound probe 143 is a device that provides for delivering ultrasound pulse trains to the targeted object and receiving of the returning ultrasound echoes, as is common practice in current ultrasound imaging systems. In FIG. 14, the probe is a cylindrical device and can either be a single or multiple element probe. Principal frequency is designed to be sufficiently high to allow much higher resolution than currently available handheld ultrasound imaging systems which are typically in the range of about 5 MHz to about 10 MHz. It is envisioned in this embodiment that the operating frequency of the probe be in the range of about 20 MHz to about 80 MHz. The focal plane of the probe is positioned at the approximate center plane of the targeted object. Advanced techniques for multiple-element annular elements are potentially used to allow for dynamic adjustment of the focal plane providing for multiple images with varying focal planes, then blended together for optimum full depth images across the entire thickness of the targeted object. Further, advanced coded excitation of the probe is used (such as chirp excitation and/or over-sampling) to further improve signal-to-noise ratio of the images particularly in the deepest parts of the scan where signal attenuation is at its highest. These advanced techniques will be important to achieving deeper imaging capability using a high frequency probe as the attenuation of the ultrasound signals in tissue are generally a function of frequency squared. It is highly desirable to use the higher operating frequency as the image resolution will increase linearly with operating frequency and thus providing much higher diagnostic value. This probe could also be a linear array and/or combined with a pivot mechanism at the probe's distal end to allow for pointing of the ultrasound beam from the end of the probe for more flexibility in optimizing scan geometry for best interface detection as disclosed in U.S. Pat. No. 9,039,623 entitled "Compound Scanning Head for an Ultrasonic Scanning Apparatus" which is incorporated herein by reference.

Control, Processing and Display System

The external pulser, motion control, signal/image processing and display system (not shown) is a system may be configured as a standalone unit on a cart or nearby table or in a more compact form attached to the portable unit itself. This system provides the means for the following functions.

A first function is to produce the excitation signals to the ultrasound probe (the pulser). These excitation signals may be for a single element or for multiple elements discussed in FIG. 16 for an annular array probe embodiment or in discussed in FIG. 17 for a linear array embodiment. Also coded excitation may be utilized for improvements in signal to noise (along with their companion compression filters in the signal processing).

A second function is to carry out all signal processing of the returning ultrasound echoes including but not limited to such things as basics amplification and filtering of raw incoming signals, A/D conversion, all digital signal processing techniques, such as Fourier conversion and filtering, compression filtering and dynamic focusing.

A third function is to carry out imaging processing to convert the processed signals into images for viewing by the healthcare professional.

A fourth function is to provide the motioning control signals to the positioner actuators.

A fifth function is to provide for storage of processed ultrasound signals and their companion images for later retrieval.

A sixth function is to provide for the storage, filtering, delivery and evacuation of the instrument fluid that surrounds the ultrasound probe during scanning.

Operation

The following is a brief description of instrument operation. A new disposable body seal is attached to the bottom of the portable instrument main body. The center of the scanning area is marked by the healthcare professional on the patient's body. The adhesive on the bottom surface of the conforming seal is exposed and the portable instrument and body seal disposable assembly are carefully positioned on the patient's skin. The positioning eyepiece is used to center the instrument on the mark on the patient's skin provided by the healthcare professional while the body seal is pressed against the body surface. In the case of the eye scanner the instrument center is aligned to the iris of the eye. Optionally a handheld stabilizing strap may be used to wrap around the torso, head or limb of choice to further stabilize the portable unit. The cable between the portable instrument and external pulser, motion control, signal/image processing and display system is then attached. Thereupon, the handheld fluid filling operation is performed by turning on the fill pump on the unit thereby transporting the instrument fluid from the reservoir to the instrument chamber. The saline fill bag attached to the disposable sealing assembly is squeezed until fluid flows from the overfill tube to the sealing chamber.

The scanning parameters on the external pulser, motion control, signal/image processing and display system are then selected. In the case of the eye scanner, a second alignment will be required by centering the Purkinje reflection of the fixation target on cornea to the center of the instrument using the eyepiece and the positioner, thereby aligning the ultrasound axis to the visual axis of the eye as disclosed in previously referenced U.S. Pat. No. 8,496,588. The patient is instructed to stay focused on the fixation target throughout the scan. When the aforementioned steps are completed, the scan sequence is initiated. The scan sequence time is typically about a second to about several seconds. The images are reviewed to determine whether a re-scan is necessary. If the scans are acceptable, the procedure is terminated by draining and discarding the saline fluid from the sealing chamber. The instrument fluid is then pumped from the instrument chamber back to the reservoir. The body seal and stabilizing strap, if used, are removed from the patient. Finally, the disposable body seal is removed from portable unit and discarded.

Annular Array Embodiment

The current disclosure is also directed towards an imaging system that provides the convenience and lower cost of ultrasound imaging systems but also with high penetration depths and resolution. This is achieved through a combination of existing ultrasound technologies and new methods for holding and stabilizing the ultrasound probe relative to the body surface.

One of the existing ultrasound technologies, annular array transducers, is described, for example, in the following two references. The first is entitled "Design and Fabrication of a 40-MHz Annular Array Transducer" by Jeffrey A. Ketterling, Orlando Aristiz'abal, Daniel H. Turnbull and Frederic L. Lizzi and is taken from IEEE Transactions on Ultrasonics, Ferroelectrics, and Frequency Control, Vol. 52, No. 4, April 2005. The second is entitled "Operational Verification of a 40-MHz Annular Array Transducer" by Jeffrey A. Ketterling, Sarayu Ramachandran and Orlando Aristiz'abal and is taken from IEEE Transactions on Ultrasonics, Ferroelectrics, and Frequency Control, Vol. 53, No. 3, March 2006.

Figure 16:
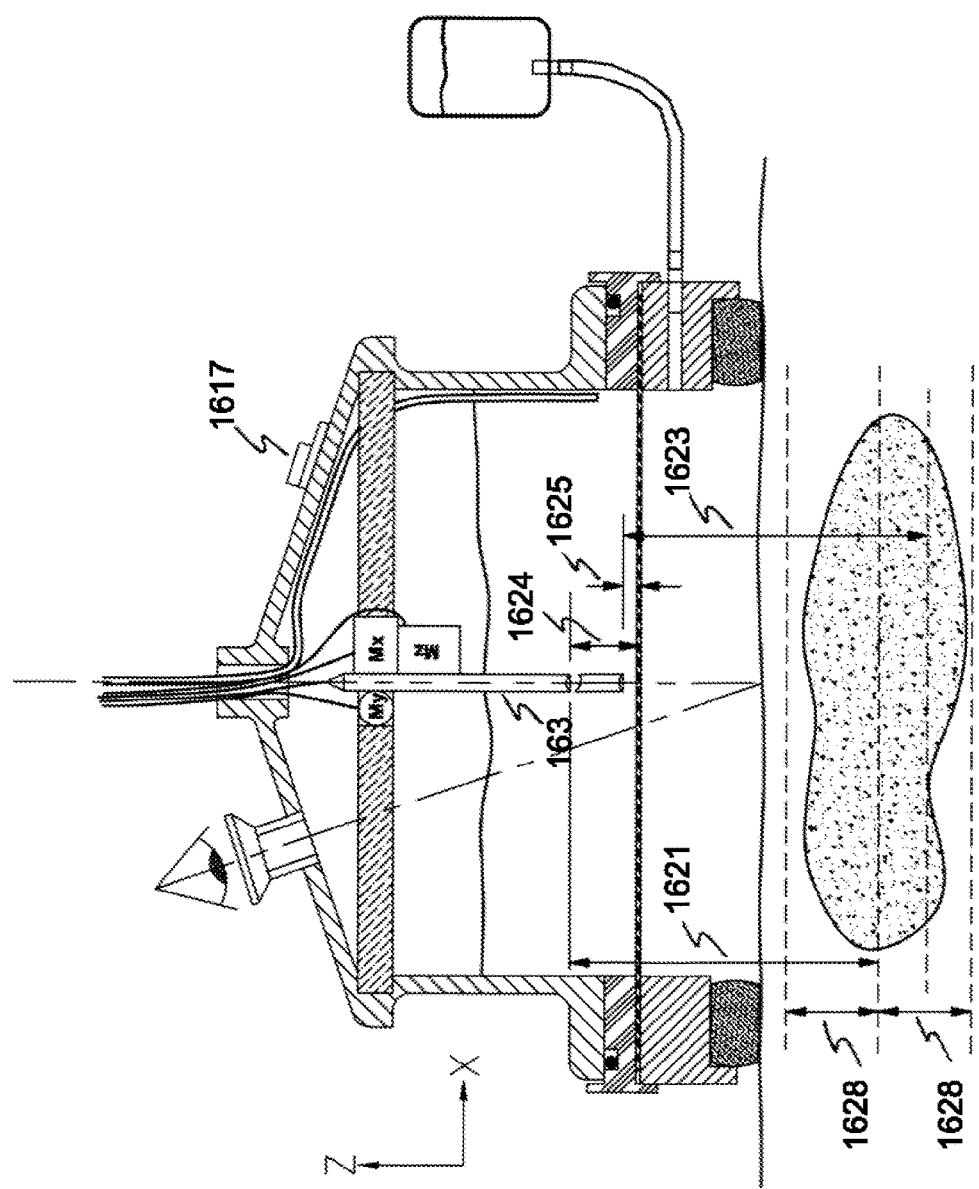
FIG. 16 is a side view of an ultrasound scanner system with an annular array ultrasound transducer.

FIG. 16 is a side view of an ultrasound scanner system with an annular array ultrasound transducer and illustrates the movement of an ultrasound annular array probe relative to body parts for extending the depth of high resolution imaging. FIG. 16 is comprised of the same components as those of FIG. 14 except that single transducer element ultrasound probe 143 is now a multi transducer element annular array probe 163. In addition, a solid state motion sensor 1617 is shown attached to the outer housing. Such sensors can measure one or more of 3 axes of acceleration, 3 axes of gyroscopic (rotational) motion, 3 axes of gravitational variation and ambient pressure. The motion sensor may be used to compensate for the effects of breathing and/or heartbeat on the relative motion between the device housing and the body part being imaged. When ultrasound probe 163 is in a position with tip distance to the membrane 1624, its focal center length is shown as length 1621 and its depth of field is two times distance 1628. For an annular array probe, the total depth of field may be approximately 5 to 6 millimeters at a center frequency of about 40 MHz. When ultrasound probe 163 is in a position with tip distance to the membrane 1625, its focal center length is shown as length 1623 and its depth of field is the same as before but centered at the new focal plane. Typically, focal length 1621 and focal length 1623 are the same.

As described below, the total high resolution image zone available by moving the ultrasound probe from tip distance to the membrane 1624 ("D1") to tip distance to the membrane 1625 ("D2"), Z-total is then computed by the formula $$Z\text{-total}=(D1-D2)+2\Delta z$$

where $\Delta z$ (distance 1628) is equal to half of the depth of field.

As noted previously, an conforming body seal and portable instrument body are disclosed that together provide for a compact yet stable fixation of the probe relative to the body surface and body part to be imaged as compared to prior art handheld ultrasound systems.

FIG. 16 illustrates the movement of an ultrasound annular array probe relative to body parts for extending the range of high resolution imaging. The elements of FIG. 16 include the following components.

The first is a z-axis positioner that allows rapid and precise setting of the distance of the ultrasound probe or array (single element, annular array or linear array) from the body surface. The z-axis actuator, Mz, is mounted on the positioner carriage. In this figure, the ultrasound probe is moved between positions D1 and D2 relative to the fluid separation membrane. The probe would be prevented from further z-axis motion past the membrane by a stop mechanism on the z-axis actuator.

The second is a y-axis positioner that allows for rapid and precise movement of the probe in the y-axis that allows for the creation of a B-Scan image.

A third is an ultrasound probe. In the case of an annular array, the depth of focus is increased through synthetic focusing to provide a much larger high resolution image zone of $2\Delta z$. This high resolution zone is a multiple of the high resolution zone of a non-synthetically focused probe as is well known to those versed in the art of ultrasound imaging.

In operation, multiple sweeps of the probe in the y-axis are taken, each with a different probe z-position. Positions D1 and D2 are auspiciously chosen so there is some overlap of the high resolution zone. These zones can be combined with known windowing techniques.

The total high resolution image zone, Z-total is then computed by the formula $$Z\text{-total} = (D1-D2) + 2\Delta z$$

It is clear that z-total can be further extended by y-axis subsequent sweeps of the ultrasound probe. However, ultimately signal to noise will degrade as the high resolution zone goes deeper into the tissue due to absorption of the ultrasound signals as it passes through a longer path length in tissue. To overcome this, well-known techniques such as coded excitation (chirp excitation as a common example) and over-sampling will be required to image tissue at ever lower signal levels in the deepest tissue.

It must be noted that above disclosed techniques all require additional scanning time. In a prior art handheld device, this becomes problematic as hand motion interferes with proper imaging. However, probe stabilization as described above provides the stabilization of the probe and time needed to optimize the combination of techniques disclosed without the limits of scanning time imposed by other handheld devices.

In the case where the best possible image quality is needed and that even breathing or heart beating produces movement that would blur the image, a solid state gyroscope and/or accelerometer could be attached to the body of the handheld device to detect these biorhythms and then make subsequent scan sweeps during the same time of each rhythm thereby eliminating this source of motion noise. Alternately, these data can be used to compensate for these biorhythms in the signal processing step.

Linear Array Embodiment

Figure 17:
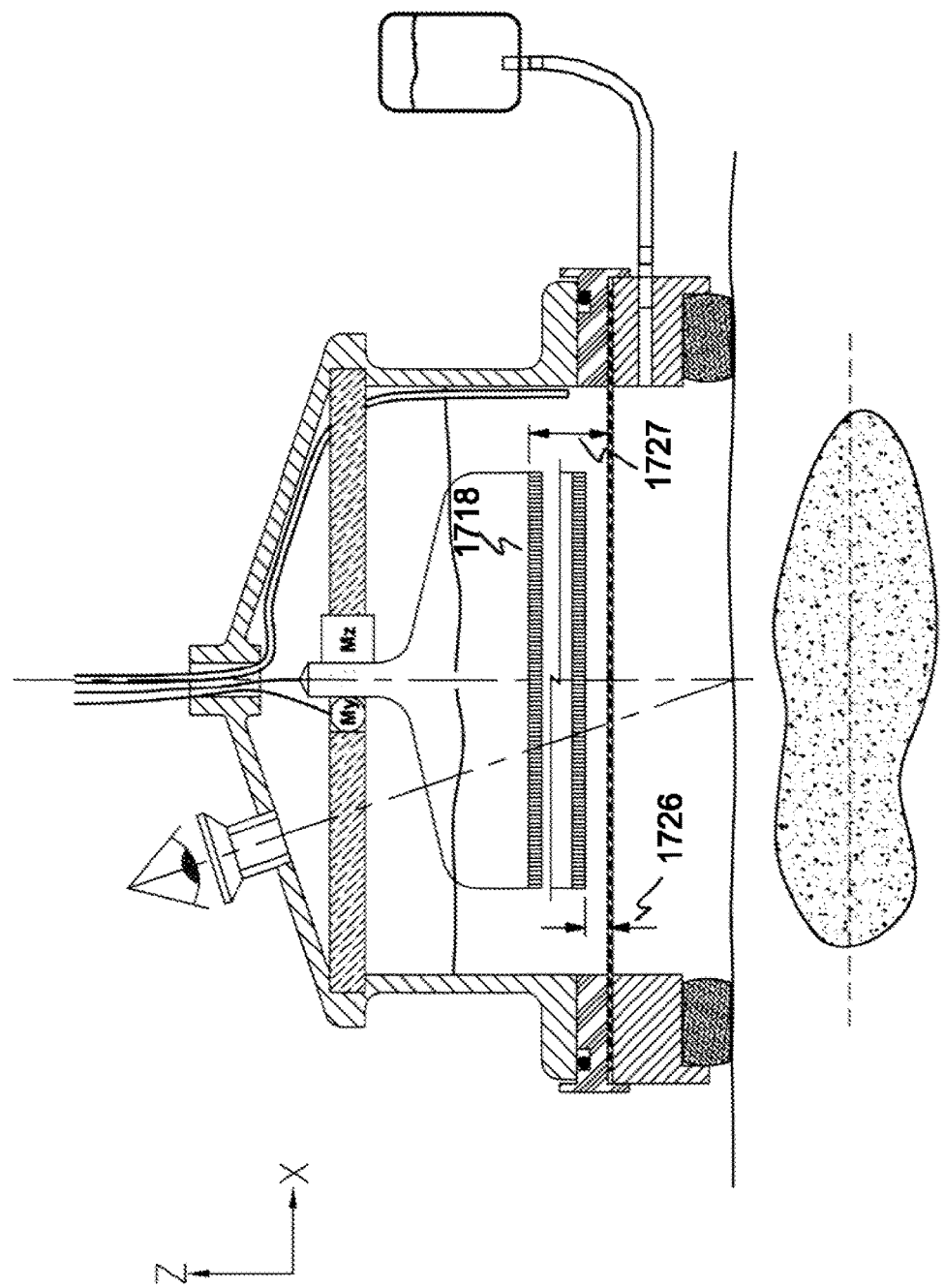
FIG. 17 is a side view of an ultrasound scanner system with a linear array of ultrasound transducers.

FIG. 17 is a side view of an ultrasound scanner system with a linear array ultrasound transducer and illustrates the movement of an ultrasound linear array relative to body parts 1726, 1727 for extending the depth of high resolution imaging. FIG. 17 is comprised of the same components as those of FIG. 14 except that the single transducer element probe or annular array probe is replaced by a 1D, 1½D or 2D linear array 1718. In addition, a solid state motion sensor such as described in FIG. 16 may be included. The linear array may be used to change focal plane location and provide beam steering capability as described below. In the simplest embodiment, the linear array may be fixed in position. In other embodiments, the linear array assembly may be moved vertically in the z-direction and/or tilted about its center point and/or moved back and forth in the x-direction and y-direction for enhanced coverage.

FIG. 17 illustrates how a linear array can be used for enhancing Z-total by the ability to be moved in the z-direction. This method could be used for eye scanning as well as scanning body parts where only a z-axis motion is necessary for enhancing high resolution image depth. Further, a phased array could also be used to synthetically angle the beam to allow best signal to noise of reflections off of key biologic interfaces that are not normal to the straight on beam or to place the effective focal plane a various depths.

By using a linear phased array in the device shown in FIG. 17, it is possible to eliminate the positioner for scanning as it would only be required for the positioning step of cen-
tering on the Purkinje reflection in case of the eye or the technician's reference mark on the body surface. The linear sweep could be duplicated with a linear array. In addition, by utilizing synthetic focusing, the outgoing beam could be tilted (using only the extreme 4-8 elements in the array as is commonly done) to obtain the effect of the pivoting head on the compound probe. Thus, we can make the desired measurements just using planar sweeps and beam tilting.

Computer Control of the Positioning and Scanning Operations

In the above-described embodiments, some components of the scanner system may utilize computer controls, processing, or storage. The first actuator Mx, second actuator My, and third actuator Mz may require controls imputing for moving or articulating ultrasound probe 143 or linear array 1718. Further, the probe 143 or linear array 1718 may require control inputs as well as processing and storage from a computer system.

In yet another embodiment, the disclosed systems and methods may be partially implemented in software that can be stored on a storage medium to include a computer-readable medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

In one embodiment, one or more computers are used to control, among other things, the rate or volume of dry product through one or more meters. In one embodiment, a user selectively inputs a volume or rate of one or more dry products through or into one or more meters. In one embodiment, the user interacts with the computer through any means known to those skilled in the art, to include a keyboard and/or display to include a touch-screen display. The term "computer-readable medium" as used herein refers to any tangible storage and/or transmission medium that participate in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored.

A number of variations and modifications of the inventions can be used. As will be appreciated, it would be possible to provide for some features of the inventions without providing others. For example, though the embodiments are discussed with reference to an arc scanning device, it is to be understood that the various embodiments may be used with other types of scanning devices, such as sector scanning devices.

The present invention, in various embodiments, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A device comprising:
   an ultrasound imaging apparatus for imaging one or more components of a body part of a patient, the ultrasound imaging apparatus comprising:
   an apparatus body comprising a first liquid chamber;
   a positioning device for positioning the body part of the patient, the positioning device interconnected to the apparatus body and comprising a second liquid chamber;
   an ultrasound transducer operable to emit ultrasound pulses and receive reflected ultrasound pulses with respect to the one or more components of the body part of the patient;
   a movable carriage supporting the ultrasound transducer;
   a guide track along which the moveable carriage moves, wherein the guide track, movable carriage and ultrasound transducer form a scan head; and
   a positioning mechanism for positioning the scan head in relation to the body part of the patient; and
   a moveable carriage location sensing device mounted on the moveable carriage, the moveable carriage location sensing device comprising one of a magnetic position encoder, an optical position encoder and a mechanical position encoder that senses a position of the moveable carriage on the guide track;
   wherein the scan head is operable in a liquid in the second liquid chamber,
   wherein the ultrasound transducer emits ultrasound pulses and receives reflected ultrasound pulses with respect to the one or more components of the body part of the patient to image the one or more components of the body part of the patient;
   wherein the positioning mechanism is configured to position the scan head back and forth along three orthogonal axes and rotate the ultrasound transducer about at least one of the three orthogonal axes;
   wherein the first liquid chamber is engaged with the body part of the patient to be imaged using a conforming seal and further comprises a membrane separating the first and second liquid chambers wherein the membrane is transparent to both ultrasound and optically transmitted and received energy pulses
   a sensor configured to detect a movement of the scan head in the three orthogonal axes; and
   a plurality of actuators interconnected to the positioning mechanism;
   wherein the plurality of actuators is configured to move the scan head in the three orthogonal axes with respect to the scan head.

2. The device of claim 1, wherein the membrane passes acoustic energy without substantial impedance, and wherein a thickness of the membrane is greater than about 10 microns.

3. The device of claim 1, wherein each of the carriage, transducer, and guide are entirely immersed in a liquid of the second liquid chamber.

4. The device of claim 3, wherein the liquid is water.

5. The device of claim 1, wherein the motion of the carriage and transducer along the guide track does not produce cavitation in the liquid of the second liquid chamber.

6. The device of claim 1, wherein the moveable carriage moves along the guide track on a bearing surface.

* * * * *